(12) United States Patent
Makino et al.

(10) Patent No.: US 11,261,484 B2
(45) Date of Patent: Mar. 1, 2022

(54) BIOMOLECULE ANALYSIS KIT AND BIOMOLECULE ANALYSIS METHOD

(71) Applicant: TOPPAN PRINTING CO., LTD., Tokyo (JP)

(72) Inventors: Yoichi Makino, Tokyo (JP); Tomoko Kunitomi, Tokyo (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 469 days.

(21) Appl. No.: 15/221,143

(22) Filed: Jul. 27, 2016

(65) Prior Publication Data

US 2016/0333400 A1 Nov. 17, 2016

Related U.S. Application Data

(63) Continuation of application No. PCT/JP2015/052803, filed on Feb. 2, 2015.

(30) Foreign Application Priority Data

Jan. 31, 2014 (JP) .............................. JP2014-017942

(51) Int. Cl.
*B01L 3/00* (2006.01)
*C12Q 1/6858* (2018.01)
(Continued)

(52) U.S. Cl.
CPC ...... *C12Q 1/6858* (2013.01); *B01L 3/502715* (2013.01); *B01L 3/502746* (2013.01);
(Continued)

(58) Field of Classification Search
None
See application file for complete search history.

(56) References Cited

U.S. PATENT DOCUMENTS

2002/0197623 A1    12/2002  Prudent et al.
2005/0118584 A1*    6/2005  Nomura .............. B01L 3/50853
                                                        435/6.16
(Continued)

FOREIGN PATENT DOCUMENTS

CN        101947124 A      1/2011
JP        2004-309405      11/2004
(Continued)

OTHER PUBLICATIONS

Chinese Office Action dated Mar. 30, 2017 in corresponding Chinese Patent Application No. 201580006310.7.
(Continued)

*Primary Examiner* — Robert T. Crow

(57) ABSTRACT

A biomolecule analysis kit includes a reaction container configured to perform an enzymatic reaction, the reaction container including a base portion which has a container-shaped portion and a low-adsorption structural portion which is provided on at least the inner surface of the container-shaped portion, the low-adsorption structural portion having an adsorption rate lower than the base portion at which at least one of a sample which becomes a target of analysis in the enzymatic reaction and a reagent for the enzymatic reaction is adsorbed thereonto, wherein a signal resulting from the enzymatic reaction is configured to be detected when the enzymatic reaction is performed in the reaction container.

16 Claims, 26 Drawing Sheets

(51) Int. Cl.
*G01N 21/64* (2006.01)
*C12Q 1/686* (2018.01)

(52) U.S. Cl.
CPC ......... *C12Q 1/686* (2013.01); *G01N 21/6428* (2013.01); *G01N 21/6452* (2013.01); *B01L 2200/0642* (2013.01); *B01L 2200/0673* (2013.01); *B01L 2200/0689* (2013.01); *B01L 2300/0829* (2013.01); *B01L 2300/0851* (2013.01); *B01L 2300/0864* (2013.01); *B01L 2300/0887* (2013.01); *B01L 2300/123* (2013.01); *B01L 2300/161* (2013.01); *B01L 2300/168* (2013.01); *B01L 2400/0487* (2013.01); *B01L 2400/086* (2013.01); *G01N 2021/6439* (2013.01)

(56) References Cited

U.S. PATENT DOCUMENTS

| | | | |
|---|---|---|---|
| 2005/0119288 A1* | 6/2005 | Bhattacharya | A61K 31/506 514/266.2 |
| 2005/0233363 A1* | 10/2005 | Harding | B01L 3/50851 435/6.16 |
| 2007/0003443 A1 | 1/2007 | Sandell | |
| 2007/0014694 A1 | 1/2007 | Beard et al. | |
| 2008/0003142 A1 | 1/2008 | Link et al. | |
| 2009/0004754 A1 | 1/2009 | Oldenburg | |
| 2009/0054809 A1* | 2/2009 | Morishita | C12Q 1/24 600/573 |
| 2009/0068757 A1* | 3/2009 | Lehmann | B01J 19/0046 436/172 |
| 2009/0099029 A1* | 4/2009 | Samuels | C07K 14/4713 506/9 |
| 2009/0258381 A1 | 10/2009 | Gorris | |
| 2010/0224494 A1 | 9/2010 | Chambers et al. | |
| 2011/0053151 A1 | 3/2011 | Hansen et al. | |
| 2011/0091989 A1 | 4/2011 | Sista et al. | |
| 2013/0165348 A1 | 6/2013 | Fujii et al. | |
| 2013/0204076 A1 | 8/2013 | Han et al. | |
| 2013/0345088 A1 | 12/2013 | Noji et al. | |

FOREIGN PATENT DOCUMENTS

| | | |
|---|---|---|
| JP | 2005-505754 | 2/2005 |
| JP | 2008-531039 | 8/2008 |
| JP | 2009-189267 | 8/2009 |
| JP | 2010-516281 | 5/2010 |
| JP | 2010-156629 | 7/2010 |
| JP | 2010-158182 | 7/2010 |
| JP | 2011-504094 | 2/2011 |
| JP | 2008-180711 | 8/2018 |
| WO | WO 2006/090987 A1 | 8/2006 |
| WO | WO 2008/091626 A1 | 7/2008 |
| WO | WO 2009/059430 A1 | 5/2009 |
| WO | WO 2011/070776 A1 | 6/2011 |
| WO | WO 2013/002193 A1 | 1/2013 |
| WO | WO 2013/176767 A1 | 11/2013 |

OTHER PUBLICATIONS

Huang Zhiyu et al., "Surface and Colloid Chemistry," Edition 2, Petroleum Industry Press, pp. 83-84, Section 5, Nonionic Surfactant, Aug. 31, 2012.
Office Action dated Jun. 6, 2018, in corresponding Chinese Patent Application No. 201580006310.7, 18 pgs.
Office Action dated Jun. 5, 2018, in corresponding Japanese Patent Application No. 2017-016262, 6 pgs.
Japanese Office Action dated Jul. 5, 2016 in corresponding Japanese Patent Application No. 2015-557255.
Extended European Search Report dated Nov. 15, 2017 in corresponding European Patent Application No. 15742996.0.
European Office Action dated Sep. 6, 2018 in corresponding European Patent Application No. 15 742 996.0.
Landegren, "Laboratory Protocols for Mutation Detection", Oxford University Press, 1996, (6 Pages).
Ahmadian et al., "A Brief History of Genetic Variation Analysis", Drug Discovery and Genomic Technologies, Biotechniques, vol. 32, No. 5, May 2002 pp. 1122-1137.
Sakakihara et al., "A Single-Molecule Enzymatic Assay in a Directly Accessible Femtoliter Droplet Array" Royal Society of Chemistry, Lab on a Chip, vol. 10, No. 24, Sep. 14, 2010, pp. 3355-3362.
Kan et al., "Isolation and Detection of Single Molecules on Paramagnetic Beads Using Sequential Fluid Flows in Microfabricated Polymer Array Assemblies", Royal Society of Chemistry, Lab on a Chip, vol. 12, No. 5, Dec. 1, 2011 pp. 977-985.
Watanabe et al., Arrayed Lipid Bilayer Chambers Allow Single-Molecule Analysis of Membrane Transporter Activity, Nature Communications, vol. 5, No. 4519, Jul. 24, 2014, pp. 1-8.
International Search Report dated Apr. 28, 2015 in corresponding International Application No. PCT/JP2015/052803.
Nomura et al., "Development of a novel nano-Invader DNA chip system," J. Biochem. Biophys. Meth., 70(5), 2007, pp. 787-795.
Japanese Office Action dated Jan. 8, 2019 in corresponding Japanese Patent Application No. 2017-016262.
Extended European Search Report dated Sep. 25, 2019 in related European Patent Application No. 19190779.9 (6 pages).
Notice of Reasons for Rejection dated Apr. 14, 2020 in Japanese Patent Application No. 2019-040985.
Reference Document 1. KrytoxTM oil/grease, [online], [search date: Apr. 2, 2020], internet, URL, http://www.maruwabussan.co.jp/businesses/products/krytox.html.
Non-Final Office Action dated Nov. 19, 2020 in U.S. Appl. No. 16/387,241.
Final Office Action dated May 11, 2021 in co-pending U.S. Appl. No. 16/387,241 (19 pages).
U.S. Appl. No. 16/387,241, filed Apr. 17, 2019, Yoichi Makino et al., Toppan Printing Co., LTD. Tokyo, JP.

* cited by examiner

FIG. 4

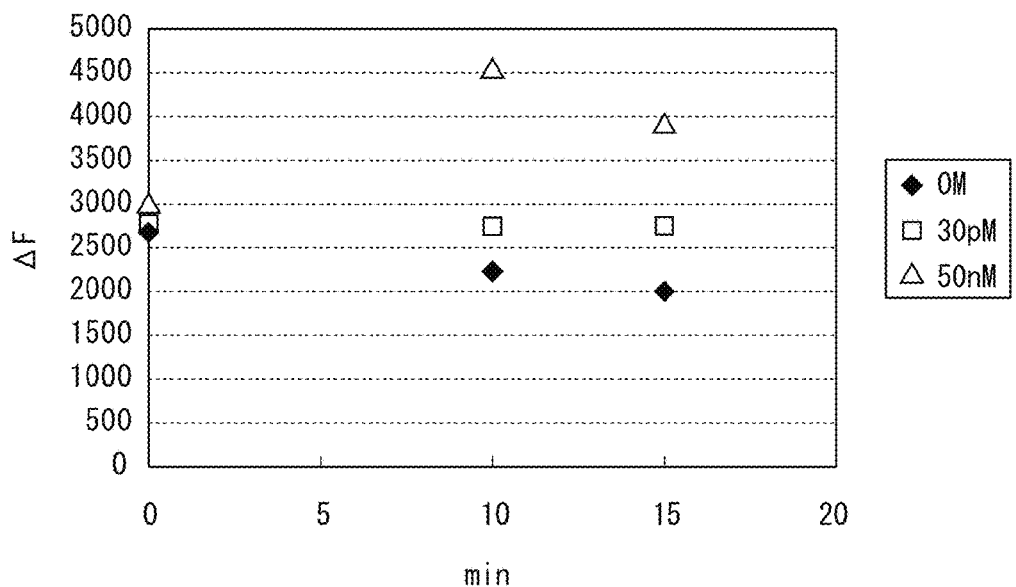

FIG. 5

|  | REACTION SYSTEM | REAGENT | REACTION AMOUNT | REACTION TIME (min) | REACTION TEMPERATURE | EVALUATION OF QUANTIFICATION PROPERTIES |
|---|---|---|---|---|---|---|
| COMPARATIVE EXAMPLE 1 | DIGITAL PCR | PCR | 1nl × MULTIPLE WELLS | 60 | NONISOTHERMAL | EXCELLENT |
| COMPARATIVE EXAMPLE 2 | PCR | PCR | 20 μl | 60 | NONISOTHERMAL | POOR |
| COMPARATIVE EXAMPLE 3 | INVADER PLUS | PCR+ INVADER | 20 μl | 60 | NONISOTHERMAL | POOR |
| COMPARATIVE EXAMPLE 4 | INVADER | INVADER | 20 μl | 120 | ISOTHERMAL | POOR |
| COMPARATIVE EXAMPLE 5 | DIGITAL ELISA | ELISA | 100Fl × MULTIPLE WELLS | 15 | ISOTHERMAL | EXCELLENT |
| EXAMPLE | DIGITAL INVADER | INVADER | 100Fl × MULTIPLE WELLS | 10 | ISOTHERMAL | EXCELLENT |

FIG. 12

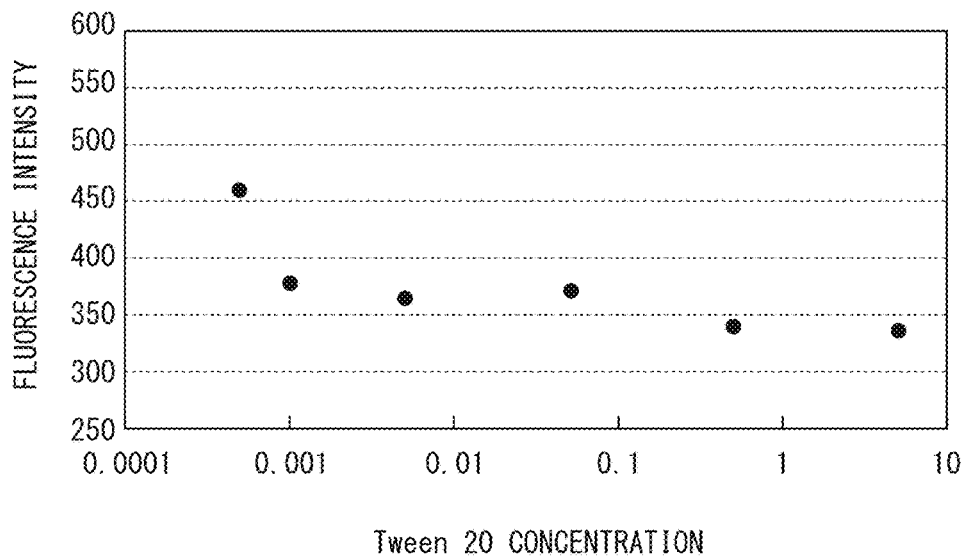

FIG. 13

| SAMPLE No. | WASHING | | REACTOIN REAGENT | | RESULT | |
|---|---|---|---|---|---|---|
| | PERFORMED/ NOT PERFOMRED | SURFACTANT | PRESENT /ABSENT | SURFACTANT | LIQUID DROPLET | REACTIVITY |
| 1 | PERFORMED | PRESENT | PRESENT | PRESENT | ○ | EXCELLENT |
| 2 | PERFORMED | PRESENT | PRESENT | ABSENT | ○ | EXCELLENT |
| 3 | PERFORMED | ABSENT | PRESENT | PRESENT | ○ | EXCELLENT |
| 4 | PERFORMED | ABSENT | PRESENT | ABSENT | △ | EXCELLENT |
| 5 | NOT PERFOMRED | — | PRESENT | PRESENT | ○ | EXCELLENT |
| 6 | NOT PERFORMED | — | PRESENT | ABSENT | × | EXCELLENT |

BIOMOLECULE ANALYSIS KIT AND BIOMOLECULE ANALYSIS METHOD

CROSS REFERENCE TO RELATED APPLICATIONS

This application is a continuation application based on a PCT Patent Application No. PCT/JP2015/052803, filed Feb. 2, 2015, whose priority is claimed on Japanese Patent Application No. 2014-017942, filed Jan. 31, 2014, the entire content of which are hereby incorporated by reference.

BACKGROUND OF THE INVENTION

Field of the Invention

The present invention relates to a biomolecule analysis kit and a biomolecule analysis method.

Description of the Related Art

It is known that a disease or a physical predisposition may be diagnosed through biomolecular analysis. For example, a physical predisposition may be diagnosed through Single Nucleotide Polymorphism (SNP) analysis, whether or not an anticancer drug will be administered may be determined through somatic mutation analysis, and infection control measures may be designed based on the analysis of the protein or DNA of viruses.

In recent years, through human genome analysis performed worldwide, sequences of about 3.1 billion base pairs of the human genome have been revealed, and it has become evident that the number of human genes is about 30,000 to 40,000. The base sequence of human beings varies between individuals, and a variation in the base sequence that exists more than 1% of a specific population is called a genetic polymorphism. Among genetic polymorphisms, SNP is considered to be associated with various diseases.

For example, genetic diseases of human beings are considered to be caused by SNP in a single gene. Furthermore, SNP in a plurality of genes is considered to affect the life style-related diseases, cancer, and the like. Therefore, it is considered that the analysis of SNP is extremely effective in the development of pharmaceutical products such as in the search for potential drug targets or the prediction of side effects. Accordingly, SNP analysis is being pushed forward as a large global project.

As one factor causing a degree of efficacy or a side effect of a drug to vary between individuals, a difference of an enzyme group involved in the drug metabolism of individuals may be exemplified. Recently, it has become evident that such a difference may also result from a slight genetic difference such as an SNP.

In recent years, a method of selecting an optimal drug by prior genetic analysis of a patient and administering it to a patient has been considered. In addition, the significance of genetic diagnosis has rapidly become highly appreciated, not only for single-gene disorders but also for multifactorial disorders. The efficacy of drugs targeting pathogenic bacteria or viruses varies between individuals in some cases even in the same species, and this variation results from minute genetic differences between individuals in many cases. It is expected that the test targets will greatly increase in the future in the genetic diagnosis of pathogenic bacteria or viruses as extrinsic factors described above.

As described above, in medical treatment of the post-genomic era, the ability to analyze for a minute genetic difference between human beings or pathogenic microorganisms, particularly, the ability to analyze for an SNP is important, and it is expected that this importance will increase in the future.

In the related art, various methods for analyzing for a minute difference in a base sequence, particularly, for analyzing for an SNP have been examined (see Landegren, Laboratory protocols for mutation detection, Oxford university press, 1996, and Ahmadian et al., Biotechniques, Vol. 32, pp 1122-1137, 2002). In order to perform analysis at a practical level, such methods are required to be excellent in all of aspects such as low cost, simplicity of the method, a short signal detection time, and accuracy of the detection result. However, a method satisfying all of the above requirements has not become known so far.

In a case where an SNP is analyzed for, generally, the sample contains only a small amount of target gene fragment. In this case, the target gene needs to be amplified in advance by a certain method. As a rapid gene amplification method with high reproducibility, a Polymerase Chain Reaction (PCR) method is well known in the related art.

Generally, in order to detect a difference of a single base of a target gene, it is necessary to perform a two-stage operation consisting of a gene amplification stage using the PCR method or the like and a stage of investigating a difference of a single base of the amplified gene. However, because this method requiring a two-stage operation includes a plurality of operations, the process thereof is complicated. Furthermore, in a PCR method, the temperature needs to be increased or decreased. Therefore, the size of a device is increased, a heat-resistant reaction container is required, and measures for preventing evaporation of the reaction solution need to be provided.

As an SNP detection method not requiring a two-stage reaction, there is an INVADER method. Because an INVADER method does not require PCR amplification and can cause an isothermal reaction, the size of a device can be reduced. However, since the INVADER method does not include a gene amplification step, a signal is slowly amplified, and the reaction needs to be performed for several hours to perform detection and determination. The INVADER method is a detection method using an enzymatic reaction. Particularly, as a method of shortening the time it takes for the signal concentration to become saturated during signal amplification using an enzyme, a method of performing a reaction in a microspace may be considered.

If the INVADER reaction is performed in a microspace, the number of molecules as a target of analysis contained in a single well can become equal to or less than 1, and the molecule as a target of analysis is seemingly in a concentrated state. Accordingly, the time taken for the signal to become saturated can be shortened. In addition, because the number of molecules to be detected that is put into a single well is equal to or less than 1, by counting the number of wells from which signals are obtained, the concentration of the molecules to be detected can be accurately ascertained.

For example, Japanese Unexamined Patent Application, First Publication No. 2004-309405 discloses that a genetic test can be performed by performing an enzymatic reaction in a microspace having a volume of equal to or less than 1 pl.

If PCR is used for SNP analysis, detection can be performed in a short time, but the constitution of the device or the procedure becomes complicated. Furthermore, in the isothermal reaction not using PCR, it takes a long time until the SNP analysis is completed, and the reactivity is low. Therefore, those methods of the related art are impractical.

SUMMARY

The present invention has been made to solve the above problems, and an object thereof is to provide a biomolecule analysis kit and a biomolecule analysis method which make it possible to rapidly and quantitatively analyze biomolecules and to improve reactivity.

A biomolecule analysis kit according to a first aspect of the present invention includes a reaction container configured to perform an enzymatic reaction, the reaction container including a base portion which has a container-shaped portion and a low-adsorption structural portion which is provided on at least the inner surface of the container-shaped portion, the low-adsorption structural portion having an adsorption rate lower than the base portion at which at least one of a sample which becomes a target of analysis in the enzymatic reaction and a reagent for the enzymatic reaction is adsorbed thereonto, wherein a signal resulting from the enzymatic reaction is configured to be detected when the enzymatic reaction is performed in the reaction container.

The low-adsorption structural portion may have a lower adsorption rate than that of the base portion at which the sample is absorbed thereonto, and a background in the signal detection may be lower than a case in which the base portion is exposed in the reaction container.

The low-adsorption structural portion may have a lower adsorption rate than that of the base portion at which the sample is absorbed thereonto, and a signal intensity in the signal detection may be higher than a case in which the base portion is exposed in the reaction container.

The reaction container may further have a modified portion formed by modifying the surface of the base portion such that the adsorption rate in the base portion within the inner surface of the container-shaped portions becomes lower than the adsorption rate in the base portion, and the container-shaped portions may have a bottomed cylindrical shape having an approximately circular opening portion having a diameter of equal to or less than 5 µm.

The reaction container may further have a low-adsorption substance layer laminated on the base portion such that the adsorption rate within the inner surface of the container-shaped portions becomes lower than the adsorption rate in the base portion, and the container-shaped portions may have a bottomed cylindrical shape having an approximately circular opening portion having a diameter of equal to or less than 5 µm.

A biomolecule analysis kit according to a second aspect of the present invention includes a reaction container configured to perform an enzymatic reaction, the reaction container including a container-shaped portion configured so that a sample that becomes a target of analysis is supplied to the container-shaped portion and a base portion in which the container-shaped portion is formed, and a reagent configured to be supplied to the reaction container and is used for the enzymatic reaction, wherein the reagent contains an adsorption inhibitor for reducing an adsorption rate of at least one of the sample and the reagent with respect to the base portion, and a signal resulting from the enzymatic reaction is configured to be detected when the enzymatic reaction is performed in the reaction container.

The enzymatic reaction may be an isothermal reaction.

The sample which becomes a target of analysis may include any one of DNA, RNA, miRNA, mRNA, and a protein, and a target substance of analysis may be any one of DNA, RNA, miRNA, mRNA, and a protein.

The target substance of analysis may be a nucleic acid, and the enzymatic reaction may be an INVADER reaction.

The reagent may generate a signal by any one of fluorescence, light emission, pH, light absorption, and electric potential.

The adsorption inhibitor may be a surfactant.

The surfactant may be a nonionic surfactant.

The nonionic surfactant may be TWEEN 20.

The nonionic surfactant may be TRITON-100.

The concentration of the surfactant may be equal to or greater than 0.0005% and equal to or less than 5%.

A biomolecule analysis method according to a third aspect of the present invention uses the biomolecule analysis kit according to the first or second aspect.

A biomolecule analysis kit according to a fourth aspect of the present invention includes a reaction container configured to perform an enzymatic reaction, the reaction container including a container-shaped portion configured so that a sample is supplied through a flow channel to the container-shaped portion and a base portion in which the container-shaped portion is formed, and a reagent configured to be supplied to the reaction container and used for the enzymatic reaction, wherein the reagent contains a surfactant for reducing the surface tension of the reagent, and fluorescence or a colorimetric signal resulting from the enzymatic reaction is configured to be detected when the enzymatic reaction is performed in the reaction container.

A biomolecule analysis method according to a fifth aspect of the present invention includes feeding a reagent into a flow channel in a reaction container which has the flow channel and a plurality of wells such that the plurality of wells is filled with the reagent; and feeding the oil sealing solution into the flow channel and sealing the reagent into the plurality of wells with an oil sealing solution, thereby forming the plurality of wells into a plurality of independent reaction containers for nucleic acid detection, wherein any one of the reagent and the oil sealing solution contains a surfactant.

The biomolecule analysis method according to the fifth aspect of the present invention may further include a step of filling the plurality of container-shaped portions with a wash buffer through the flow channel before filling the plurality of wells with the reagent.

A biomolecule analysis method according to a sixth aspect of the present invention is a biomolecule analysis method using the biomolecule analysis kit according to the first, second, or fourth aspect, in which after the wash buffer is supplied to the container-shaped portion, the reagent is supplied to the container-shaped portion.

According to the above aspects of the present invention, a biomolecule analysis kit and a biomolecule analysis method which makes it possible to rapidly and quantitatively analyze biomolecules and to improve reactivity can be provided.

BRIEF DESCRIPTION OF THE DRAWINGS

FIG. 4 is a graph showing the results of a fluorescence intensity measurement test in the first example of the present invention.

FIG. 5 is a table showing the results of a reaction time measurement test in the first example of the present invention.

FIG. 12 is a graph showing the results of a fluorescence intensity measurement test in the second example of the present invention.

FIG. 13 is a view showing the operation and effect of the biomolecule analysis method according to the second embodiment of the present invention.

DETAILED DESCRIPTION OF THE PREFERRED EMBODIMENTS

First Embodiment

Hereinafter, a biomolecule analysis kit and a biomolecule analysis method according to a first embodiment of the present invention will be described with reference to FIGS. 1 and 2.

Figure 1:
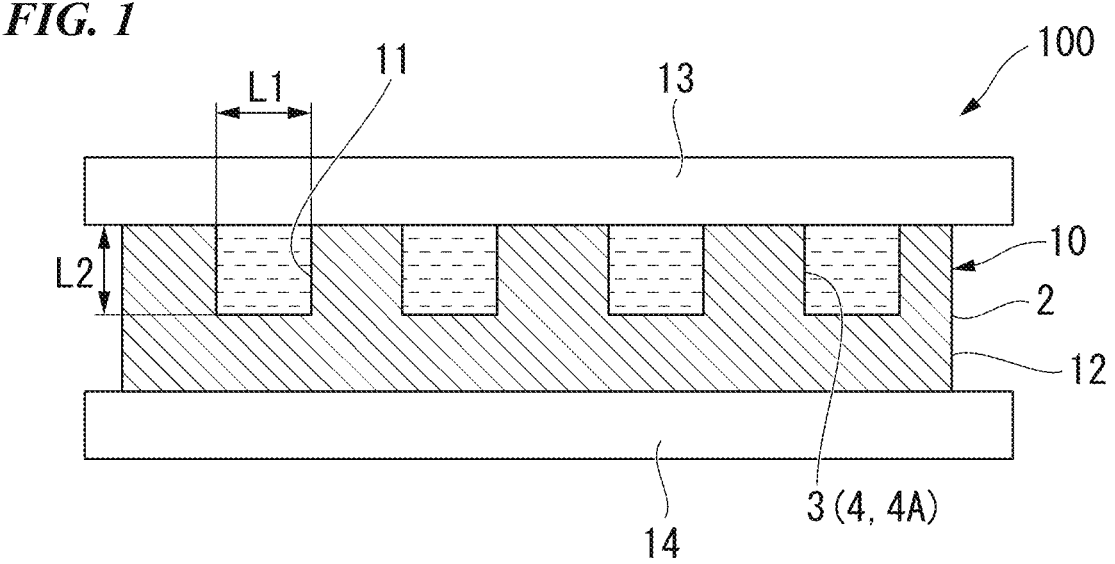
FIG. 1 is a sectional view of a biomolecule analysis kit applied to a biomolecule analysis method according to a first embodiment of the present invention.

FIG. 1 is a sectional view of the biomolecule analysis kit to which the biomolecule analysis method according to the present embodiment is applicable. In the biomolecule analysis kit according to the present embodiment, as a biomolecule to be analyzed, any of DNA, RNA, miRNA, mRNA (hereinafter, referred to as RNAs in some cases), and a protein is selected.

As shown in FIG. 1, a biomolecule analysis kit 100 includes a soft flat plate 12 and a glass substrate 14 that constitute a reaction container 10 and a cover glass 13 that can seal off the reaction container 10.

The reaction container 10 has a base portion 2 which is formed to have microspaces 11 (container-shaped portions) each having a bottomed cylindrical shape with one open end and low-adsorption structural portions 3 which are provided on the surface of the base portion 2.

By preparing the microspaces 11 in the soft flat plate 12 formed of polydimethylsiloxane (PDMS) by means of imprinting, the reaction container 10 is formed.

The microspace 11 constituting the reaction container 10 is a space having a bottomed cylindrical shape with an opening portion at one end. The microspace 11 has a diameter L1 of 5 µm and a depth L2 of 5 µm, for example. For instance, the microspace 11 has a volume of about 100 femtoliters (fl). In the reaction container 10, an array of a plurality of microspaces 11 is formed. That is, the microspaces 11 are arrayed in the reaction container 10.

For example, on the 5 mm×5 mm rectangular surface of the soft flat plate 12, the microspaces 11 are arrayed in the form of a lattice along each side of the surface. The size of a gap between the microspaces 11 is set according to the resolution by which a signal can be independently detected in each of the microspaces 11.

The volume of each microspace 11 may be appropriately set. However, the smaller the volume of the microspace 11, shorter the reaction time until a signal becomes detectable. For example, the volume of the microspace 11 is equal to or less than 100 picoliters (pl).

Specifically, in a case where the aim is to shorten the time taken for generating a sufficient signal by saturating the signal, the volume of the microspace 11 is set based on a liquid amount in which the number of biomolecules as a target of analysis becomes equal to or less than 1 per well.

The soft flat plate 12 is formed on the glass substrate 14, for example. The thickness of the glass substrate 14 is appropriately set in consideration of a point that the glass substrate 14 needs to have a sufficient strength in a process of forming the plurality of microspaces 11 by means of imprinting by using the soft flat plate 12 as a material.

In the present embodiment, the low-adsorption structural portions 3 have the following constitution, for example.

Constitutional Example 1

In each low-adsorption structural portion 3, a region positioned on the inner surface of the microspace 11 of the reaction container 10 within the surface of the base portion 2 is hydrophobic. For instance, each low-adsorption structural portion 3 has a modified portion 4 formed by modifying the surface of the base portion 2 to be hydrophobic.

Constitutional Example 2

Each low-adsorption structural portion 3 has a low-adsorption substance layer 4A in a region positioned on the inner surface of the reaction container 10 within the surface of the base portion 2. The low-adsorption substance layer 4A is formed of a material to which a sample as a target of analysis using the biomolecule analysis kit 100 of the present embodiment or a reagent for the analysis exhibits a low adsorption rate. For example, the low-adsorption substance layer 4A is a hydrophobic coat.

Examples of the low-adsorption substance layer 4A also include a polymer coat having a molecular structure that does not allow the permeation of a fluorescent substance. The polymer coat preferably has a molecular structure denser than that of PDMS described above. By inhibiting the permeation of a fluorescent substance, the polymer coat exerts an effect of preventing the decrease of signal intensity. For substances other than PDMS, based on the molecular structure of the substance that becomes the material of the base portion 2, a polymer coat having a molecular structure that can prevent the permeation of a reagent may be selected. Such a polymer coat inhibits a decrease of signal intensity.

The polymer coat in the low-adsorption structural portions 3 is not limited to the coat inhibiting the permeation of a fluorescent substance, and a coat that inhibits the permeation of a substance involved in an enzymatic reaction may be appropriately selected according to the reagent to be used.

Next, the composition of the reagent which can be suitably used in the biomolecule analysis kit 100 according to the present embodiment will be described.

In the present embodiment, each reagent contains an adsorption inhibitor, and accordingly, the constituents of the reagent can be prevented from being adsorbed onto the inner surface of the reaction container 10 of the biomolecule analysis kit 100.

For example, the adsorption inhibitor has a composition containing at least one kind of component among a surfactant, phospholipid, and other polymer compounds, and any materials may be used by being mixed together. Examples of the surfactant include a nonionic surfactant. Examples of the nonionic surfactant include TWEEN, glycerol, TRITON-X100, and the like. Examples of the polymer compounds include polyethylene glycol (PEG), DNA, and a protein.

Examples of the adsorption inhibitor as a mixture of two or more kinds of material include an adsorption inhibitor obtained by mixing phospholipid with PEG In a case where a nonionic surfactant is used as the surfactant, the concentration of the nonionic surfactant contained in the reagent is preferably equal to or less than 5%. In a case where TWEEN 20 is used, the concentration of TWEEN 20 contained in the reagent is preferably within a range of equal to or greater than 0.0005% and equal to or less than 5%, and more preferably within a range of equal to or greater than 0.001% and equal to or less than 0.5%. If the concentration of TWEEN 20 is equal to or greater than 0.0005%, the reactions caused in the plurality of microspaces 11 can be independently detected, and the fluorescence from the microspaces 11 can be accurately measured. If the concentration of TWEEN 20 is equal to or less than 5%, a sufficient enzymatic reaction is obtained.

The adsorption inhibitor described above may be a substance adsorbed onto the inner surface of the microspace 11 in the reaction container 10. By supplying the adsorption inhibitor-containing reagent into the reaction container 10, the adsorption inhibitor is adsorbed onto the inner surface of the reaction container 10. As a result, compared to a case where the reagent does not contain the adsorption inhibitor, the enzyme used for the enzymatic reaction, the nucleic acid or protein that becomes a target of analysis, the labeling substance used for signal detection, and the like are hardly adsorbed onto the inner surface of the reaction container 10.

In a case where oil is put into the microspaces 11, the adsorption inhibitor may be added to the oil to be used.

It is preferable that the adsorption inhibitor is contained in at least any one of the reagents coming into contact with the inside of the reaction container 10 during the period between a time before at least one of the enzyme used for the enzymatic reaction, the nucleic acid or protein that becomes a target of analysis, the labeling substance used for signal detection, and the like is initially supplied into the reaction container 10 and a time when the signal detection is ended. For example, the adsorption inhibitor may be mixed with a solvent such as a buffer solution for diluting the reagent at a predetermined concentration.

The adsorption inhibitor may be contained in all of the reagents coming into contact with the inside of the reaction container 10 during the period between a time before at least one of the enzyme used for the enzymatic reaction, the nucleic acid or protein that becomes a target of analysis, the labeling substance used for signal detection, and the like is initially supplied into the reaction container 10 and a time when the signal detection is ended.

The adsorption inhibitor is preferably a substance that does not hinder an enzymatic reaction or a signal amplification reaction.

Next, a biomolecule analysis method using the biomolecule analysis kit 100 according to the present embodiment will be described. FIG. 2 is a flowchart showing the biomolecule analysis method according to the present embodiment.

Figure 2:
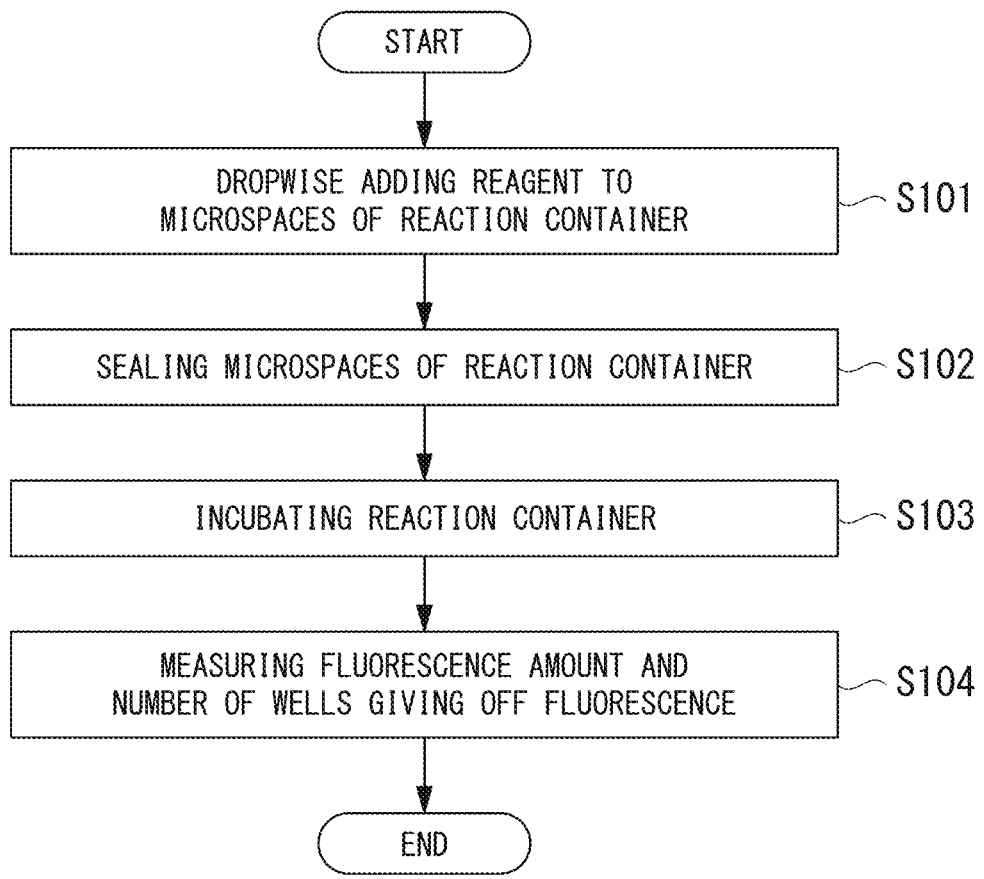
FIG. 2 is a flowchart of the biomolecule analysis method according to the first embodiment of the present invention.

First, a reagent containing a substance (DNA in the present embodiment, for example) that becomes a target of analysis is added dropwise to the microspaces 11 of the reaction container 10 (Step S101 shown in FIG. 2). Specifically, the reagent added dropwise in the present embodiment contains an INVADER reaction reagent (1 µM allele probe, 0.4 µM INVADER oligo, 1 µM FAM-labeled arm, 20 mM MOPS pH 7.5, 15 mM NaCl, 6.25 mM $MgCl_2$, and 50 U/µL cleavase) and DNA.

The liquid amount of the reagent added dropwise to the microspaces 11 of the reaction container 10 may be appropriately set according to the number of microspaces 11. Furthermore, the liquid amount and concentration of the reagent added dropwise to the microspaces 11 of the reaction container 10 are adjusted such that approximately single DNA molecule is put into each of the microspaces 11. For example, in the present embodiment, the liquid amount of the reagent added dropwise to the microspaces 11 of the reaction container 10 is 0.5 µL in total, and 0.5 µL of the liquid is distributed into the plurality of microspaces 11.

Then, the microspaces 11 of the reaction container 10 are covered with the cover glass 13 (Step S102 shown in FIG. 2). As a result, each of the microspaces 11 becomes an independent reaction chamber filled with the INVADER reaction reagent and DNA. Thereafter, the reaction container 10 in which the microspaces 11 are filled with the INVADER reaction reagent and DNA is incubated in an oven at 62° C., for example (Step S103 shown in FIG. 2). Through the incubation, signal amplification performed in an isothermal INVADER reaction suitably proceeds.

Subsequently, the reaction container 10 in which each of the microspaces 11 is filled with the INVADER reaction reagent and DNA is taken out after a preset time, and the number of wells emitting fluorescence and the fluorescence amount thereof are measured (Step S104 shown in FIG. 2).

In the present embodiment, a detection system may also be adopted which detects, in addition to fluorescence, emission of visible light, color development, a change in pH, a change in electric potential, or the like as a signal. In addition, the constitution of the present embodiment can be adopted for analyzing proteins.

Second Embodiment

Hereinafter, a biomolecule analysis kit and a biomolecule analysis method according to a second embodiment of the present invention will be described with reference to FIG. 6. A biomolecule analysis kit 100A according to the present embodiment includes an array device 20 for nucleic acid quantification, reagent, and an oil sealing solution.

Figure 6:
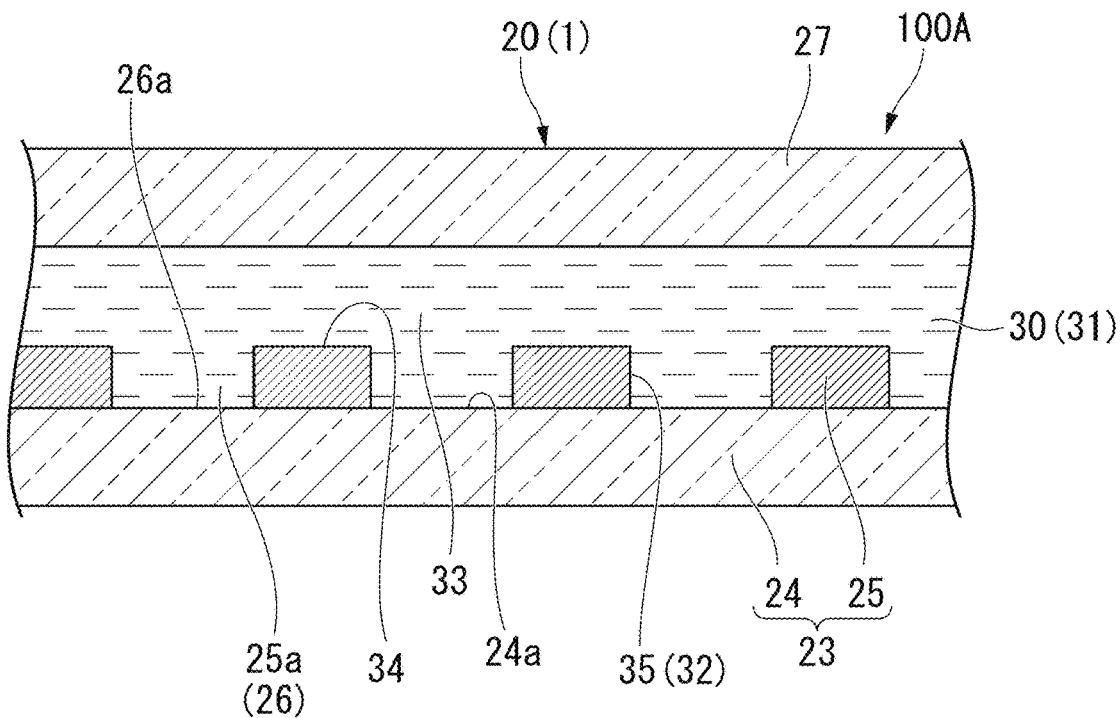
FIG. 6 is a sectional view of a biomolecule analysis kit applied to a biomolecule analysis method according to a second embodiment of the present invention.

FIG. 6 is a sectional view of the array device 20 for nucleic acid quantification according to the present embodiment. In the biomolecule analysis kit according to the present embodiment, as a biomolecule to be analyzed, any of DNA, RNA, miRNA, mRNA (hereinafter, referred to as RNAs in some cases), and a protein is selected.

As shown in FIG. 6, the array device 20 for nucleic acid quantification includes a reaction container 30, a cover portion 27, an inlet portion (not shown in the drawing), and an outlet portion (not shown in the drawing). The reaction container 30 includes a base portion 23 and a flow channel 31. In the base portion 23, a plurality of wells (container-shaped portions) 26, a substrate 24, and a micropore array layer 25 are formed.

The micropore array may be formed directly in the substrate 24. Alternatively, a member in which the micropore array is formed may be fixed to the substrate 24 by means of adhesion, welding, or the like.

The substrate 24 is a plate-like member formed of a material that is substantially transparent. The material of the substrate 24 is a resin or glass, for example. Specifically, the substrate 24 may be formed of polystyrene or polypropylene. The substrate 24 should have such a stiffness that the substrate is not broken at the time of handling due to a device for transporting the array device 20 for nucleic acid quantification or a manual operation of an operator.

The micropore array layer 25 is a layer in which a plurality of through holes 25a arranged in a line. The thickness of the micropore array layer 25 is 3 µm, and there is a clearance of 100 µm between the micropore array layer 25 and the cover portion 27. Each of the through holes 25a is a bottomed cylindrical space having an opening portion at one end, and has a diameter of 5 µm (the through hole 25a has a cylindrical shape 3 µm long in the centerline direction). For example, the volume of the through hole 25a is about 60 femtoliters (fl).

The volume of each through hole 25a may be appropriately set. However, the smaller the volume of the through hole 25a, the further the reaction time taken until a signal becomes detectable can be shortened.

For example, the volume of each through hole 25a is equal to or less than 100 picoliters.

In the present embodiment, a detection system may also be adopted which detects, in addition to fluorescence, emission of visible light, color development, a change in pH, a change in electric potential, or the like as a signal. In addition, the constitution of the present embodiment can be adopted for analyzing proteins.

The distance (pitch) between the center lines of the through holes 25a should be longer than the diameter of each of the through holes 25a.

The size of the interval (gap) between the through holes 25a is set according to the resolution by which a signal can be independently detected in each of the through holes 25a.

The through holes 25a are arranged to form a triangular lattice shape with respect to the micropore array layer 25.

The way the through holes 25a are arranged is not particularly limited. In the base portion 23, bottomed cylindrical micro-wells 26 (container-shaped portions) in which the substrate 24 becomes a bottom surface portion 26a are formed by the through holes 25a formed in the micropore array layer 25 and a surface 24a of the substrate 24.

Specifically, in a case where the aim is to shorten the time taken for generating a sufficient signal by saturating the signal, the volume of each well 26 is set based on a liquid amount in which the number of biomolecules as a target of analysis becomes equal to or less than 1 per well.

The material of the micropore array layer 25 may be a resin, glass, and the like, and may be the same as or different from the material of the substrate 24. Furthermore, the micropore array layer 25 and the substrate 24 may be integrated by the same material. In addition, the micropore array layer 25 and the substrate 24 may be integrally molded with the same material. Examples of the material of the micropore array layer 25 formed of a resin include a cycloolefin polymer, silicon, polypropylene, polycarbonate, polystyrene, polyethylene, polyvinyl acetate, a fluorine resin, an amorphous fluorine resin, and the like. These are merely examples of the material of the micropore array layer 25, and the material of the micropore array layer 25 is not limited thereto.

The micropore array layer 25 may be colored. If the micropore array layer 25 is colored, in a case where optical measurement such as the measurement of fluorescence, light emission, absorbance, and the like is performed in the wells 26, the influence of light from other wells 26 adjacent to a well 26 that becomes a measurement target can be reduced.

By performing processing such as etching, embossing, or cutting on the solid pattern of a hydrophobic coat laminated on the substrate 24, the through holes 25a are formed on the micropore array layer 25. In a case where the micropore array layer 25 and the substrate 24 are integrally molded, by performing processing such as etching, embossing, or cutting on the substrate 24, the portions corresponding to the through holes 25a of the micropore array layer 25 are formed. In this way, a pattern having a hydrophobic portion and a hydrophilic portion can be formed on the substrate.

The cover portion 27 is superposed on the base portion 23 such that the cover portion 27 covers opening portions of the plurality of wells 26 in a state where a gap is formed between the base portion 23 and the cover portion 27. The space between the base portion 23 and the cover portion 27 becomes a flow channel 31 through which various liquids flow. In the present embodiment, through the space between the base portion 23 and the cover portion 27, various liquids flow from the inlet portion toward the outlet portion.

Next, the composition of the reagent which can be suitably used in the biomolecule analysis kit 100A according to the present embodiment will be described.

Figure 7:
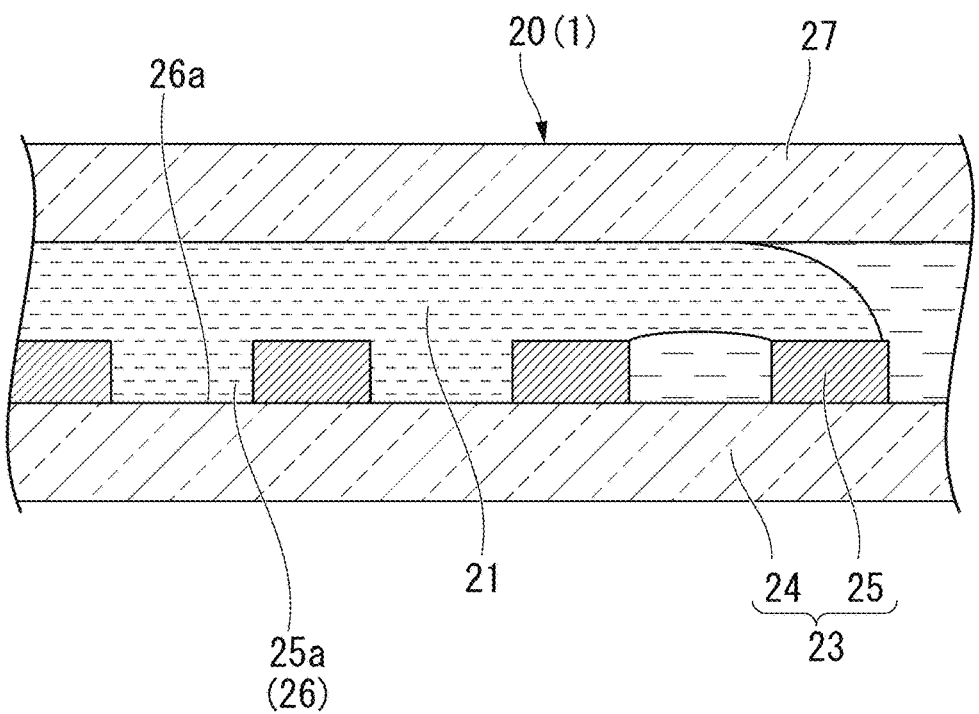
FIG. 7 is a sectional view of the biomolecule analysis kit applied to the biomolecule analysis method according to the second embodiment of the present invention.
Figure 8:
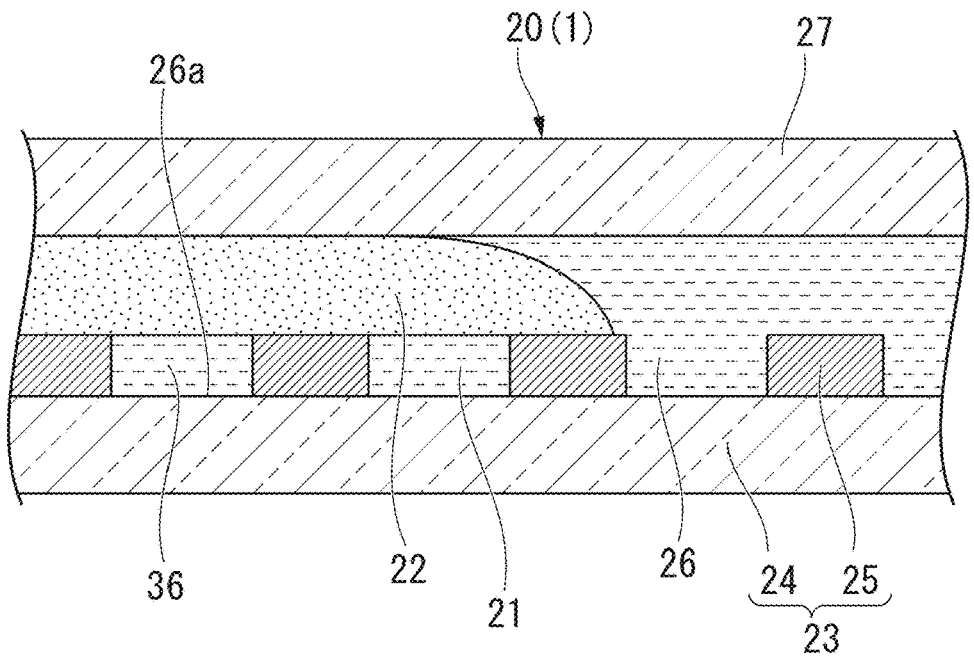
FIG. 8 is a sectional view of the biomolecule analysis kit applied to the biomolecule analysis method according to the second embodiment of the present invention.

As shown in FIGS. 7 and 8, a detection reaction reagent 21 is a solution which can be fed into the space between the base portion 23 and the cover portion 27 from the inlet portion. The detection reaction reagent 21 is a reagent for causing a biochemical reaction such as an enzymatic reaction with regard to a target substance of analysis.

The biochemical reaction to a target substance of analysis is a reaction by which signal amplification may occur in the presence of a nucleic acid in a case where the target substance of analysis is DNA (nucleic acid), for example. The detection reaction reagent 21 is selected according to the method which can detect a nucleic acid, for example. For instance, the reagents used in an INVADER (registered trademark) method, a LAMP (registered trademark) method, a TAQMAN (registered trademark) method, a fluorescent probe method, or other methods are included in the detection reaction reagent 21 of the present embodiment.

In the present embodiment, when the target substance of analysis is a nucleic acid, the nucleic acid can be detected without performing a nucleic acid amplification step as in the PCR method as in the related art. However, if necessary, a product obtained by amplifying the nucleic acid as a target of analysis by the PCR method or the like may be used as a sample.

Furthermore, even when the target substance of analysis is other than a nucleic acid, the present embodiment can be applied after the substance is appropriately pre-treated as necessary such that it becomes applicable to the present embodiment.

In the present embodiment, at least one of the reagents contains the adsorption inhibitor, and as a result, the constituents of the reagent can be prevented from being adsorbed onto the inner surface of the wells 26 of the biomolecule analysis kit 100A. All of the reagents may contain the adsorption inhibitor.

Examples of the reagents include a buffer, a detection reaction reagent, a sample (a substance as a target of analysis: DNA, RNAs, a protein, or the like) solution, a sealing solution, and a solvent for diluting a reagent or a sample.

For example, the adsorption inhibitor has a composition containing at least one kind of component among a surfactant, phospholipid, and other polymer compounds, and any materials may be used by being mixed together. Examples of the surfactant include a nonionic surfactant. Examples of the nonionic surfactant include TWEEN, glycerol, TRITON-X100, and the like. Examples of the polymer compounds include polyethylene glycol (PEG), DNA, and a protein.

Examples of the adsorption inhibitor as a mixture of two or more kinds of materials include an adsorption inhibitor obtained by mixing phospholipid with PEG In a case where a nonionic surfactant is used as the surfactant, the concentration of the nonionic surfactant contained in a reagent is preferably equal to or less than 5%. In a case where TWEEN 20 is used, the concentration of TWEEN 20 contained in a reagent is preferably within a range of equal to or greater than 0.0005% and equal to or less than 5%, and more preferably within a range of equal to or greater than 0.001% and equal to or less than 0.5%. If the concentration of TWEEN 20 is equal to or greater than 0.0005%, the reactions caused in the plurality of wells 26 can be independently detected, and the fluorescence from the wells 26 can be accurately measured. If the concentration of TWEEN 20 is equal to or less than 5%, a sufficient enzymatic reaction is obtained.

The surfactant is not limited to the nonionic surfactant, and an ionic surfactant (an anionic, cationic, or amphoteric surfactant) may be used as the surfactant. A mixture of ionic surfactants or a mixture of an ionic surfactant and a nonionic surfactant may also be used.

Furthermore, a mixture of a surfactant and a polymer compound can also be used as the adsorption inhibitor.

Next, the composition of the oil sealing solution 22 which can be suitably applied to the biomolecule analysis kit 100A according to the present embodiment will be described.

In the present embodiment, for the purpose of preventing the constituents of the reagent from being adsorbed onto the inner surface of the wells 26 of the biomolecule analysis kit 100A, the adsorption inhibitor may be contained in the oil sealing solution 22.

The oil sealing solution 22 (see FIG. 8) is a solution which can be fed into the space between the base portion 23 and the cover portion 27 from the inlet portion. The oil sealing solution 22 can be selected from the materials which are immiscible with the sample containing the target substance of analysis. As the oil sealing solution 22, mineral oil, FC40 as a fluorine-based liquid, or the like can be used.

Furthermore, in the present embodiment, for the purpose of preventing the constituents of the reagent from being adsorbed onto the inner surface of the wells 26 of the biomolecule analysis kit 100A, a wash buffer for wells may be fed into the kit before the reagent is fed into the kit. The buffer may contain the adsorption inhibitor.

The adsorption inhibitor may be a substance adsorbed onto the inner surface of the wells 26 in the reaction container 30. By supplying the adsorption inhibitor-containing reagent into the reaction container 30, the adsorption inhibitor is adsorbed onto the inner surface of the reaction container 30. As a result, compared to a case where the reagent does not contain the adsorption inhibitor, the enzyme used for the enzymatic reaction, the nucleic acid or protein that becomes a target of analysis, the labeling substance used for signal detection, and the like are hardly adsorbed onto the inner surface of the reaction container 30.

The adsorption inhibitor contained in the wash buffer may be a nonionic surfactant. Examples of the nonionic surfactant include TWEEN, glycerol, TRITON-X100, and the like. Furthermore, the wash buffer may constitute a portion of the reagent.

It is preferable that the adsorption inhibitor is contained in at least one of the reagents coming into contact with the inside of the reaction container 30 during the period between a time before at least one of the enzyme used for the enzymatic reaction, the nucleic acid or protein that becomes a target of analysis, the labeling substance used for signal detection, and the like is initially supplied into the reaction container 30 and a time when the signal detection is ended. For example, the adsorption inhibitor may be mixed with a solvent such as a buffer solution for diluting the reagent at a predetermined concentration.

The adsorption inhibitor may be contained in all of the reagents coming into contact with the inside of the reaction container 30 during the period between a time before at least one of the enzyme used for the enzymatic reaction, the nucleic acid or protein that becomes a target of analysis, the labeling substance used for signal detection, and the like is initially supplied into the reaction container 10 and a time when the signal detection is ended.

The adsorption inhibitor is preferably a substance that does not hinder an enzymatic reaction or a signal amplification reaction.

Figure 9:
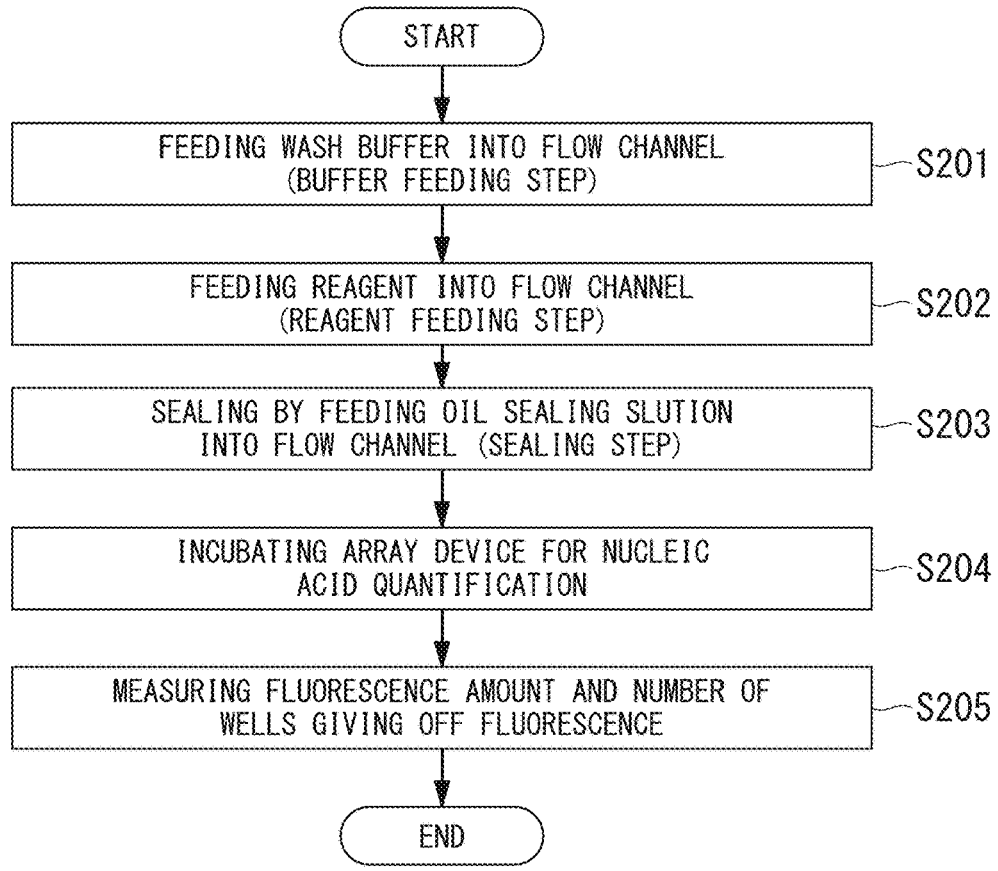
FIG. 9 is a flowchart showing the biomolecule analysis method according to the second embodiment of the present invention.

Next, a biomolecule analysis method using the biomolecule analysis kit 100A according to the present embodiment will be described. FIG. 9 is a flowchart showing the biomolecule analysis method according to the present embodiment.

First, the inlet portion and the outlet portion not shown in the drawing are opened, and a wash buffer 33 containing the adsorption inhibitor is fed into the gap between the base portion 23 and the cover portion 27 through the inlet portion by a dispensing pipette, for example (Step S201 shown in FIG. 9). The buffer 33 spreads across the gap between the base portion 23 and the cover portion 27 so as to cover all of the plurality of wells 26 (see FIG. 6). As a result, within the surface of the base portion 23, low-adsorption structural portions 32 having a low-adsorption substance layer 35 is formed in a region positioned on the inner surface of the through hole 25a and a region 34 positioned between wells adjacent to each other.

The reaction container 30 may be filled in advance with the buffer 33 instead of being fed with the buffer 33. In this case, the inlet portion and the outlet portion may be sealed with a film or the like such that the buffer 33 is sealed in the reaction container 30.

Then, a reagent containing a substance (in the present embodiment, DNA for example) that becomes a target of analysis is fed into the gap between the base portion 23 and the cover portion 27 through the inlet portion by a dispensing pipette, for example (Step S202 shown in FIG. 9). Specifically, the reagent that fills the kit in the present embodiment contains an INVADER reaction reagent (the detection reaction reagent 21) (1 µM allele probe, 1 µM of INVADER oligo, 1 µM FAM-labeled arm, 10 mM MOPS pH 7.5, 6.25 mM $MgCl_2$, and 50 U/µL cleavase, and Tween 20) and DNA which is a target substance of analysis. The reagent spreads across the gap between the base portion 23 and the cover portion 27 so as to cover all of the plurality of wells 26 (see FIG. 7). The reagent is fed into the gap between the base portion 23 and the cover portion 27, and as a result, the buffer 33 is discharged from the outlet portion. At this time, if the color of the reagent is different from that of the buffer 33, it is easy to ascertain into which portion the reagent has been fed within the space between the base portion 23 and the cover portion 27.

As shown in FIG. 6, in the flow channel 31 formed by the base portion 23 and the cover portion 27, the plurality of wells 26 formed by the substrate 24 and the micropore array layer 25 is arranged. As the reagent is flowed into the wells 26, the buffer 33 that fills the plurality of wells 26 is sequentially replaced with the reagent.

However, some of the wells 26 retain the buffer 33 on the inner surface thereof. In this case, the buffer 33 that fills the plurality of wells 26 is not replaced with the reagent, and the reagent is superposed on the buffer 33. However, because the buffer 33 and the reagent are easily intermixed, after the reagent is superposed on the buffer 33, the solute in the reagent is diffused into the buffer 33. Therefore, in both of the well in which the buffer is replaced with the reagent and the well in which the reagent is superposed on the buffer 33, substantially the same reaction occurs.

The amount of liquid that fills the wells 26 may be appropriately set according to the number of through holes 25a. Furthermore, the amount and concentration of the liquid added dropwise to the wells 26 are adjusted such that approximately single DNA molecule is put into each well 26. For example, in the present embodiment, the amount of liquid that fills the wells 26 is 0.5 µL for the entirety of the reaction container, and 0.5 µL of the liquid is distributed into the plurality of wells 26.

Thereafter, as shown in FIG. 8, from the inlet portion, the oil sealing solution 22 is fed into the flow channel 31 formed by the base portion 23 and the cover portion 27. In a state where the reagent has been distributed into the buffer, the oil sealing solution 22 seals the liquid in the plurality of wells 26, and as a result, the plurality of well 26 becomes a plurality of independent reaction chambers 36 (reaction containers for nucleic acid detection). That is, in the present embodiment, because the oil sealing solution 22 covers each of the wells 26, each of the wells 26 becomes independent from each other similarly to the microspaces disclosed in the first embodiment. Furthermore, in the gap between the base portion 23 and the cover portion 27, the oil sealing solution 22 pushes the liquid on the outside of the plurality of wells 26 out of the outlet portion (Step S203 shown in FIG. 9).

Then, the array device 20 in which each of the wells 26 is filled with the INVADER reaction reagent and DNA is incubated in an oven at 62° C., for example (Step S204 shown in FIG. 9). By the incubation, signal amplification performed in an isothermal INVADER reaction suitably proceeds.

Subsequently, the array device 20 in which each of the wells 26 is filled with the INVADER reaction reagent and DNA is taken out after a preset time, and the number of wells giving off fluorescence and the amount of fluorescence are measured (Step S205 shown in FIG. 9).

That is, the biomolecule analysis method using the biomolecule analysis kit 100A according to the present embodiment includes a step (reagent feeding step) of feeding a reagent into a flow channel in a reaction container having the flow channel and a plurality of container-shaped portions such that the plurality of wells is filled with the reagent, and a step (sealing step) of sealing the reagent in the plurality of wells with an oil sealing solution by feeding the oil sealing solution into the flow channel after the reagent feeding step such that the plurality of wells becomes a plurality of independent reaction containers for nucleic acid detection.

In the present embodiment, a detection system may also be adopted which detects, in addition to fluorescence, emission of visible light, color development, a change in pH, a change in electric potential, or the like as a signal. In addition, the constitution of the present embodiment can be adopted for analyzing proteins.

In the present embodiment, each reagent contains the adsorption inhibitor, and accordingly, the constituents of the reagent can be prevented from being adsorbed onto the inner surface of the reaction container 30 of the biomolecule analysis kit 100A. The adsorption inhibitor may be contained in all of the reagents or some of the reagents.

The reagents may contain a substance reducing the surface tension of the constituents of the reagents instead of the adsorption inhibitor. For example, a surfactant reduces the surface tension of the reagents. Accordingly, in order to fill each of the wells with the reagents, it is effective for the reagents to contain a surfactant.

EXAMPLES

First Example

Figure 3:
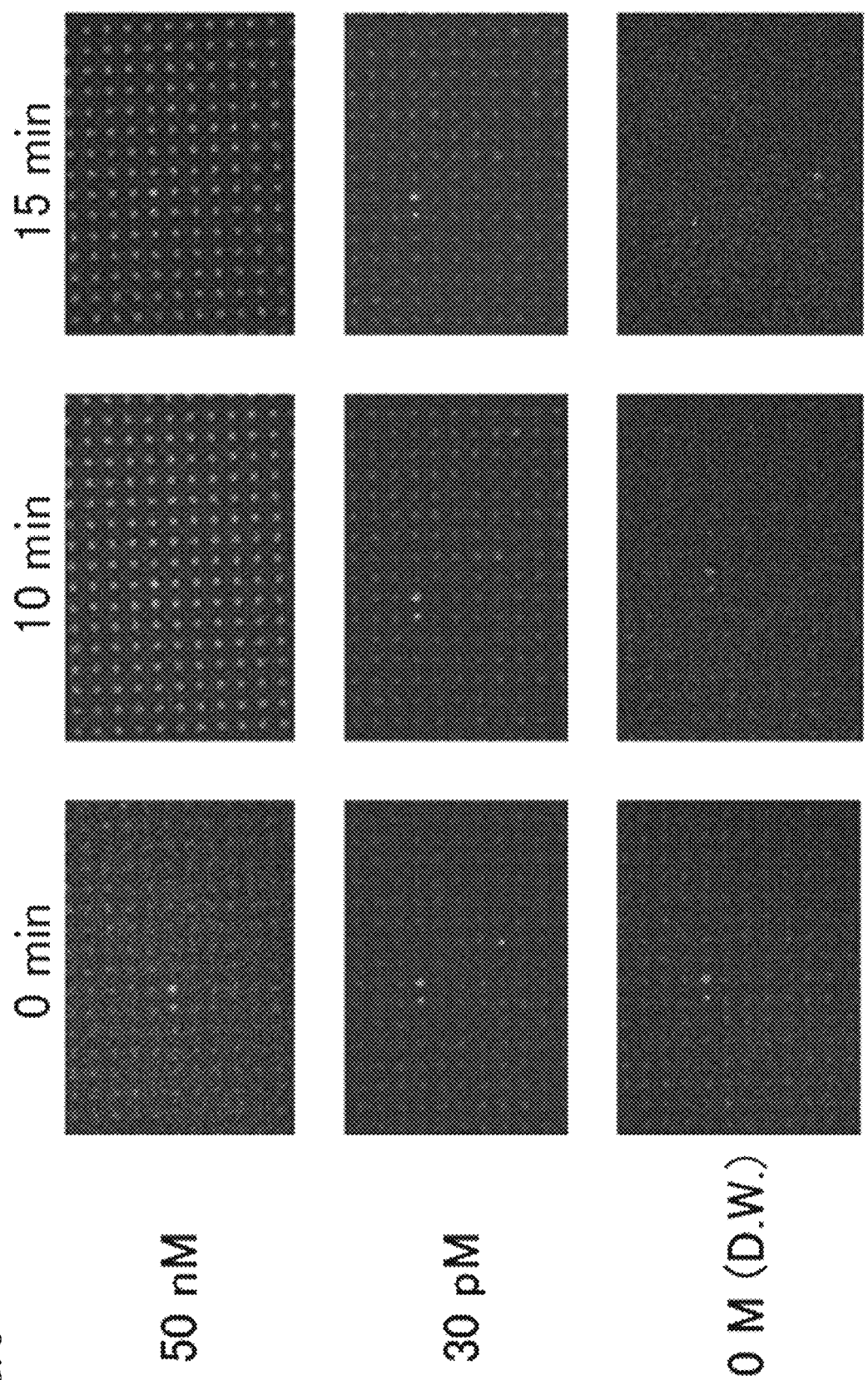
FIG. 3 shows fluorescence images showing the results of a fluorescence amount measurement test in a first example of the present invention.

Next, an example demonstrated for checking the operation and effect of the biomolecule analysis method according to the first embodiment of the present invention will be described. FIG. 3 shows fluorescence images showing the results of a fluorescence amount measurement test in the present example. FIG. 4 is a graph showing the results of a fluorescence intensity measurement test in the present example. In FIG. 4, the abscissa shows the reaction time, and the ordinate shows the fluorescence intensity. FIG. 5 is a table showing the results of a reaction time measurement test in the present example. In FIG. 5, "Excellent" means that the quantification properties are excellent, and "Poor" means that the quantification properties are poor in the present example.

<Test of Counting Number of Wells Giving Off Fluorescence>

First, the microspaces 11 of the reaction container 10 were filled with the INVADER reaction reagent and 3 kinds of artificial synthetic DNA. At this time, the concentration of the artificial synthetic DNA was set to be 30 pM at which a single molecule was put into a single well, 50 nM at which 1,666 molecules were put into a single well, and 0 M at which no molecule was put into a single well.

Then, the reaction container 10 was incubated in an oven at 62° C., and after 0 minute (0 min), 10 minutes (10 min), and 15 minutes (15 min), the condition of the reaction container 10 was checked.

As shown in FIG. 3, if the DNA concentration is equal to or greater than 30 pM, the fluorescence amount varies in almost all of the microspaces 11 with respect to the background observed in a case where the DNA concentration is 0 M, and it is understood that DNA is present.

<Fluorescence Intensity Measurement Test>

Next, the reaction container 10 filled with the artificial synthetic DNA set as above was incubated in an oven at 62° C. Furthermore, in order to check the condition of the reaction container after 0 minutes, 10 minutes, and 15 minutes, images of 5 wells were selected at each DNA concentration, and the average of the fluorescence amount of 21 pixels in each image was determined. Herein, the wells after the reaction were measured using a fluorescence microscope (ZEISS, AX10), an object lens (EC Plan-Neofluar 40× oil NA 1.3), a light source (LEJ, FluoArc00 1.26A Usable with HBO 10), a sensor (Hamamatsu Photonics K.K., EM-CCD C9100), a filter (OLYMPUS CORPORATION, U-MNIBA2), and analysis software (Hamamatsu Photonics K.K., AQUACOSMOS 2.6: exposure time 64.3 ms, EM gain 180, offset 0, binning X1).

As shown in FIG. 4, when the DNA concentration was 30 pM at which a single molecule was accommodated in a single microspace 11, the fluorescence with intensity distinguishable from the case where the DNA concentration was 0 M was detected.

<Reaction Time Measurement Test>

Thereafter, the reaction time in the analysis method of the related art was compared with the reaction time in the analysis method of the present invention. For the reaction time measurement test, as methods compared with the present invention, a method of performing a digital PCR reaction using a reagent in an amount of 1 nanoliter (nl)× multiple wells (Comparative example 1), a method of performing a PCR reaction using a reagent in an amount of 20 microliters (μl) (Comparative example 2), a method of performing PCR+INVADER reaction using a reagent in an amount of 20 μl (Comparative example 3), a method of performing an INVADER reaction using a reagent in an amount of 20 μl (Comparative example 4), and a method of performing a digital ELISA reaction using a reagent in an amount of 100 femtoliters (fl)×multiple wells (Comparative example 5) were adopted.

As shown in FIG. 5, the reaction time measurement test revealed that in Comparative example 1 in which a digital PCR reaction was performed using a reagent in an amount of 1 nl×multiple wells, 60 minutes were consumed as the reaction time, the temperature condition was nonisothermal, and the quantification properties were excellent. In Comparative example 2 in which a PCR reaction was performed using a reagent in an amount of 20 μl, 60 minutes were consumed as the reaction time, the temperature condition was nonisothermal, and the quantification properties were not excellent. In Comparative example 3 in which PCR+INVADER reaction were performed using a reagent in an amount of 20 μl, 60 minutes were consumed as the reaction time, the temperature condition was nonisothermal, and the quantification properties were not excellent.

In Comparative example 4 in which an INVADER reaction was performed using a reagent in an amount of 20 μl, 120 minutes were consumed as the reaction time, the temperature condition was isothermal, and the qualification properties were not excellent. In Comparative example 5 in which a digital ELISA reaction was performed using a reagent in an amount of 100 fl×multiple wells, 15 minutes were consumed as the reaction time, the temperature condition was isothermal, and the quantification properties were excellent.

In contrast, in the present example in which a digital INVADER reaction was performed using a reagent in an amount of 100 fl×multiple wells, only 10 minutes were consumed as the reaction time, the temperature condition was isothermal, and the quantification properties were excellent. Therefore, it has become evident that because a digital INVADER reaction was performed using a reagent in an amount of 100 fl×multiple wells in the present example, the above excellent results were obtained.

Second Example

Figure 10:
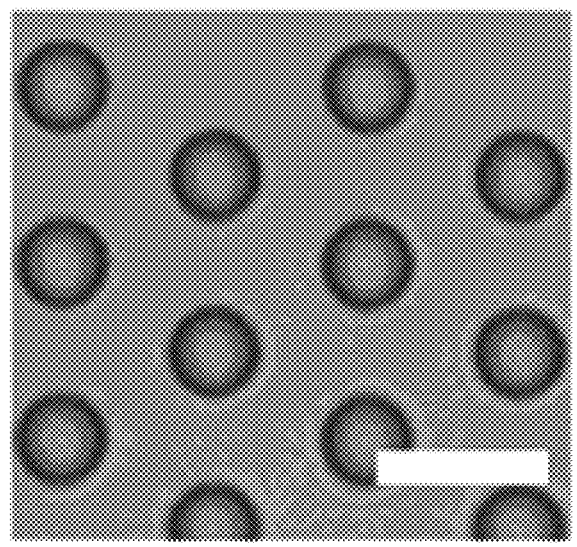
FIG. 10 is an electron micrograph showing wells in a second example of the present invention.
Figure 11A:
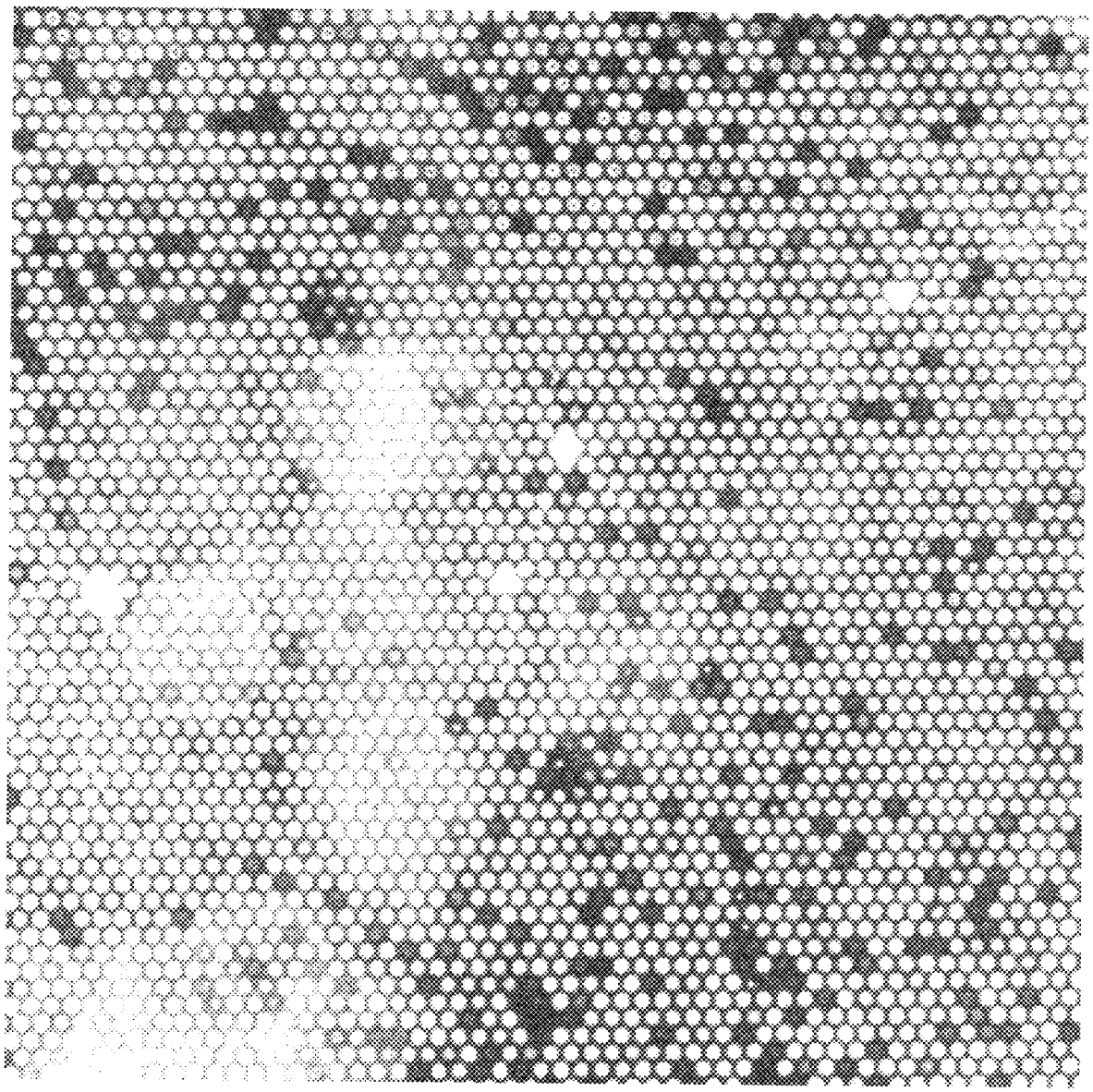
FIG. 11A is a fluorescence image showing the result of a fluorescence amount measurement test performed in the second example of the present invention under the conditions of a concentration of TWEEN 20 of 0% and a heating time of 10 minutes.
Figure 11B:
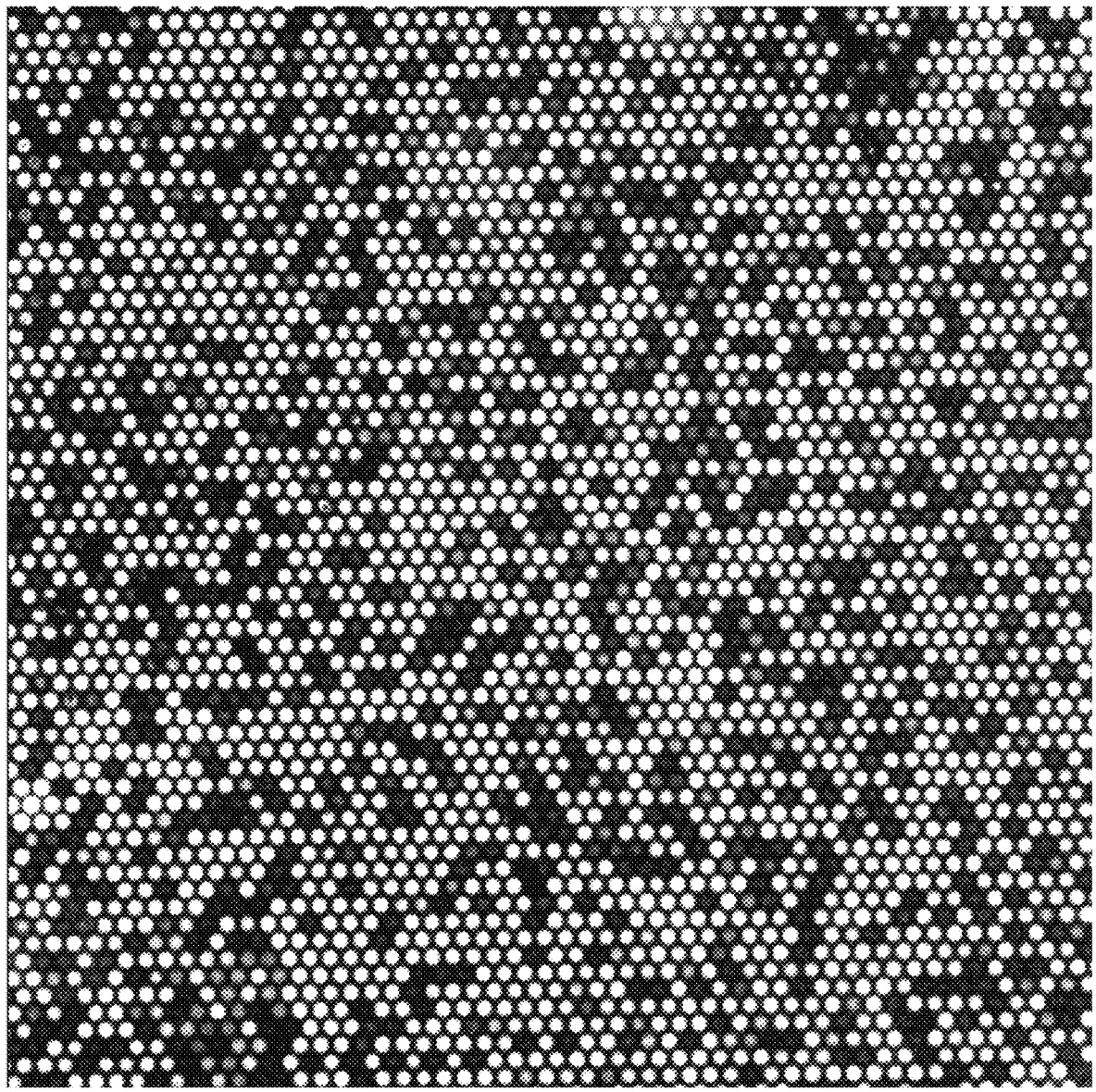
FIG. 11B is a fluorescence image showing the result of the fluorescence amount measurement test performed in the second example of the present invention under the conditions of a concentration of TWEEN 20 of 0.0005% and a heating time of 10 minutes.
Figure 11C:
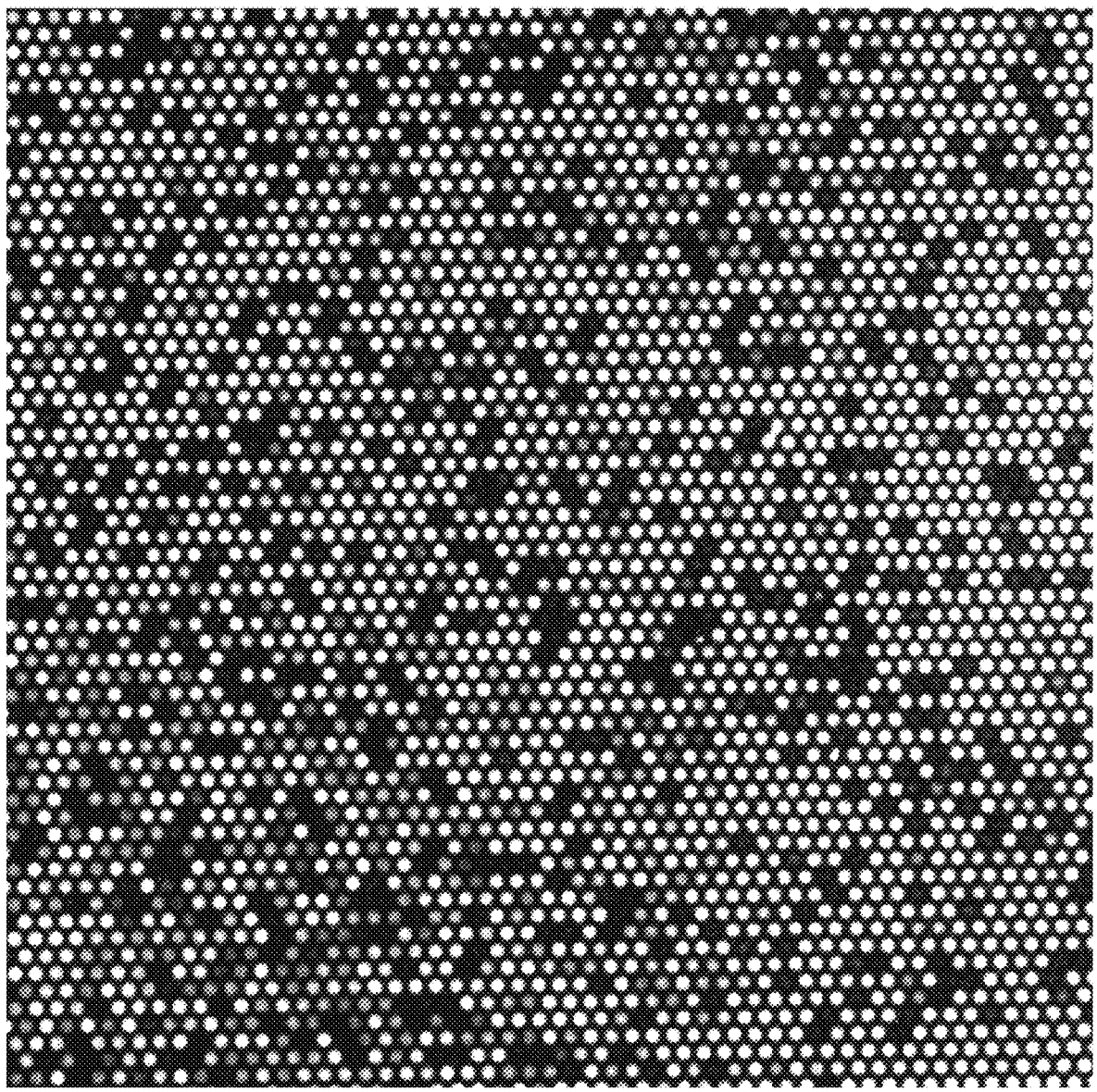
FIG. 11C is a fluorescence image showing the result of the fluorescence amount measurement test performed in the second example of the present invention under the conditions of a concentration of TWEEN 20 of 0.001% and a heating time of 10 minutes.
Figure 11D:
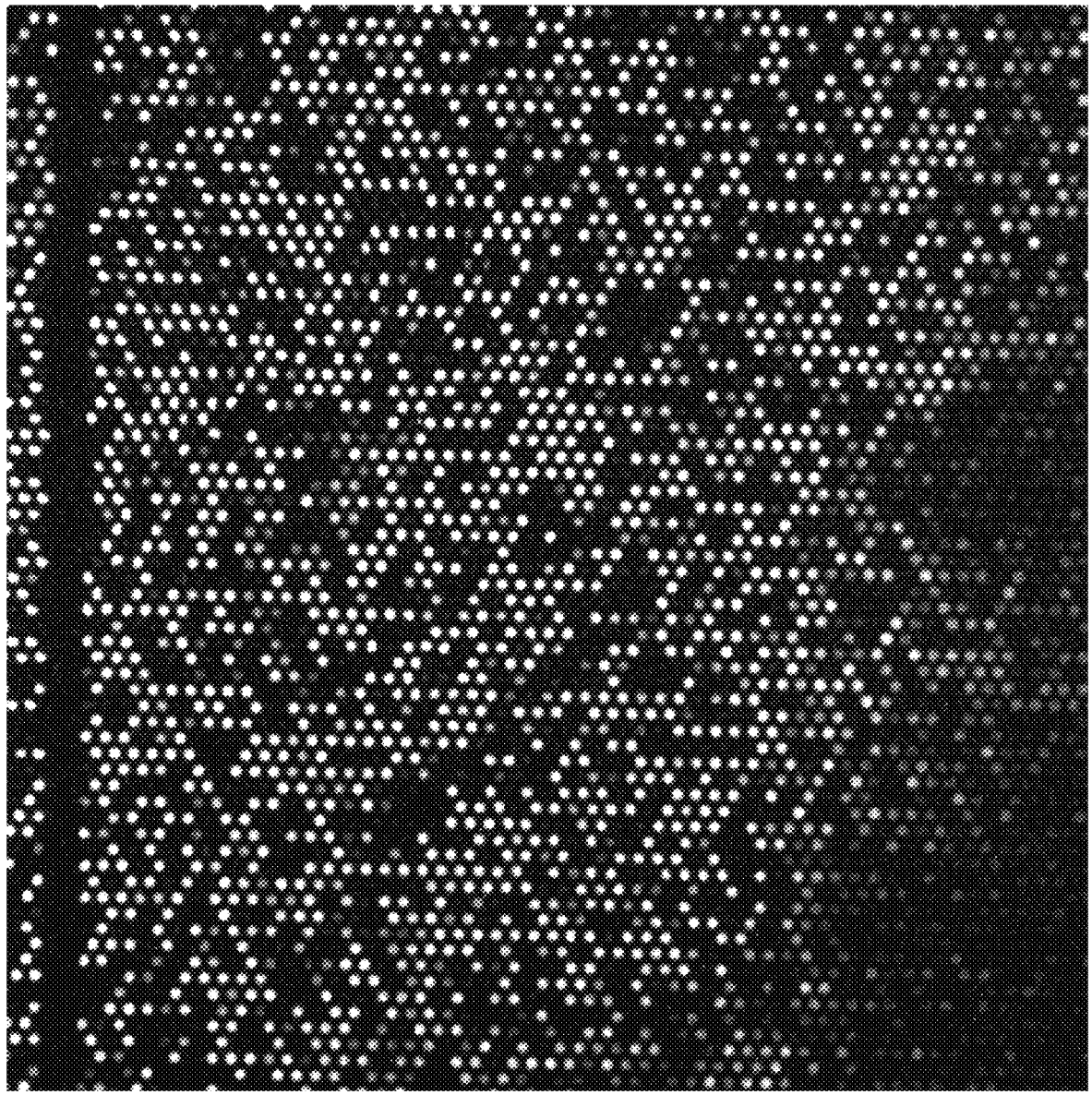
FIG. 11D is a fluorescence image showing the result of the fluorescence amount measurement test performed in the second example of the present invention under the conditions of a concentration of TWEEN 20 of 0.005% and a heating time of 10 minutes.
Figure 11E:
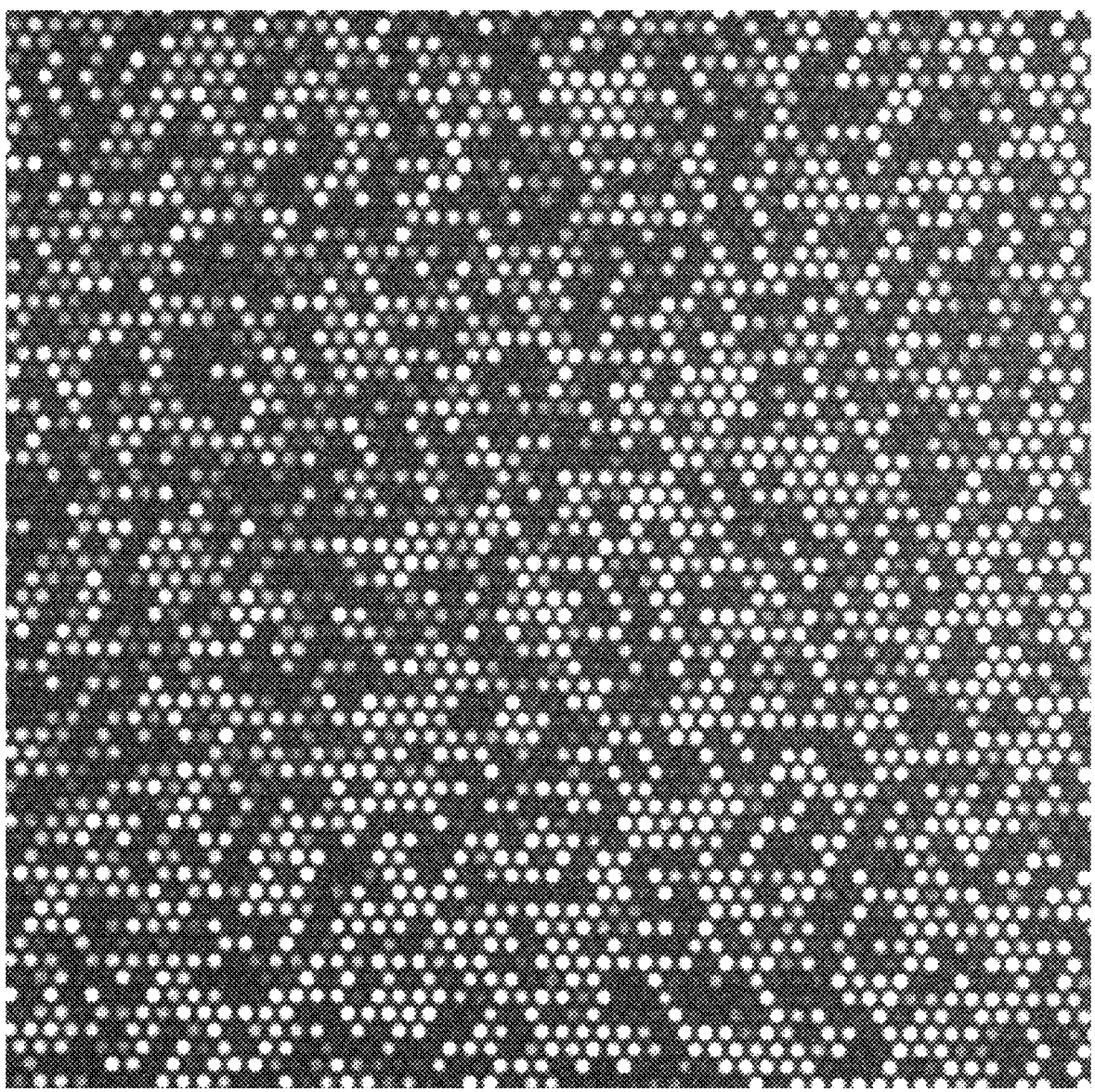
FIG. 11E is a fluorescence image showing the result of the fluorescence amount measurement test performed in the second example of the present invention under the conditions of a concentration of TWEEN 20 of 0.05% and a heating time of 10 minutes.
Figure 11F:
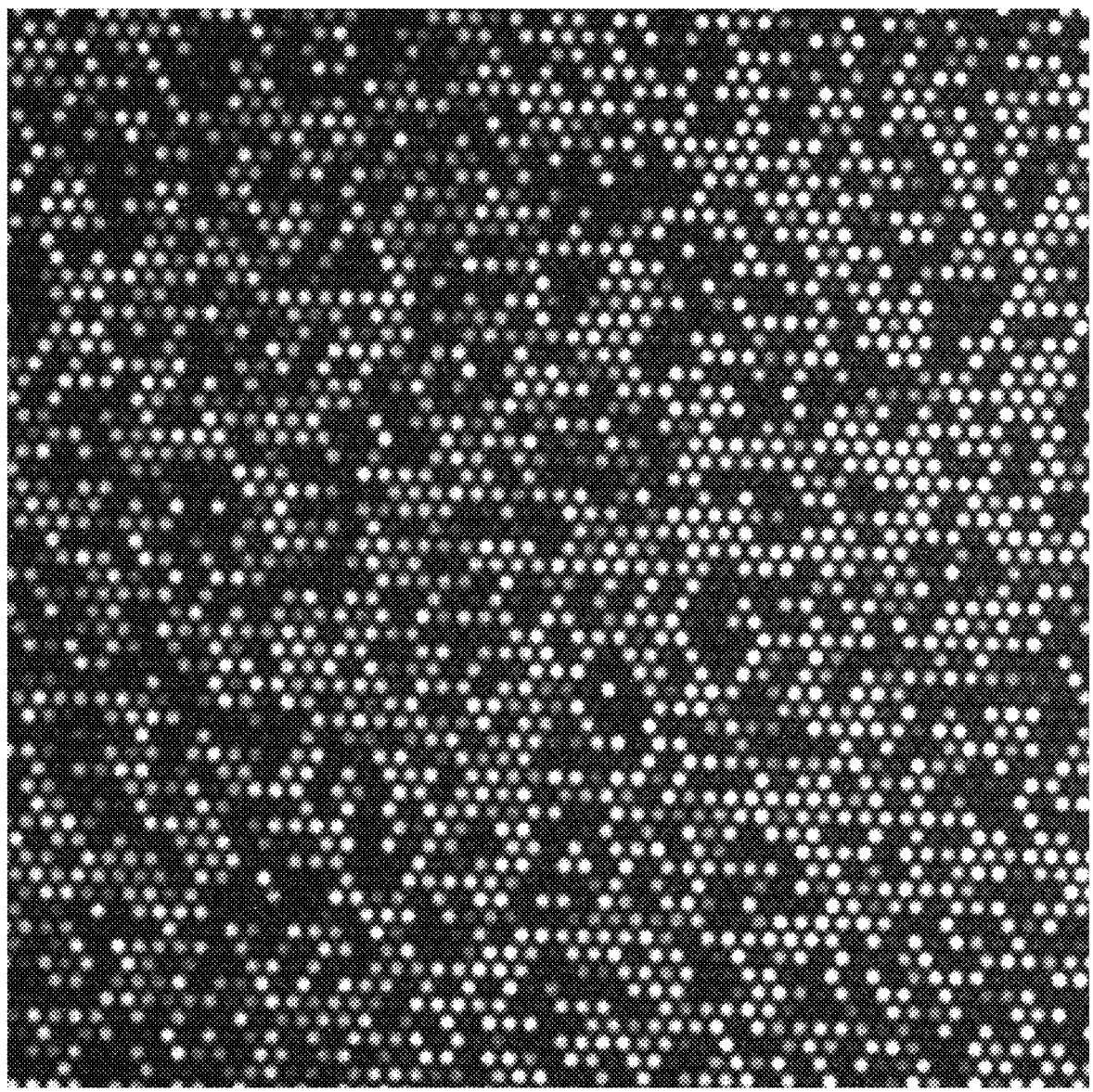
FIG. 11F is a fluorescence image showing the result of the fluorescence amount measurement test performed in the second example of the present invention under the conditions of a concentration of TWEEN 20 of 0.5% and a heating time of 10 minutes.
Figure 11G:
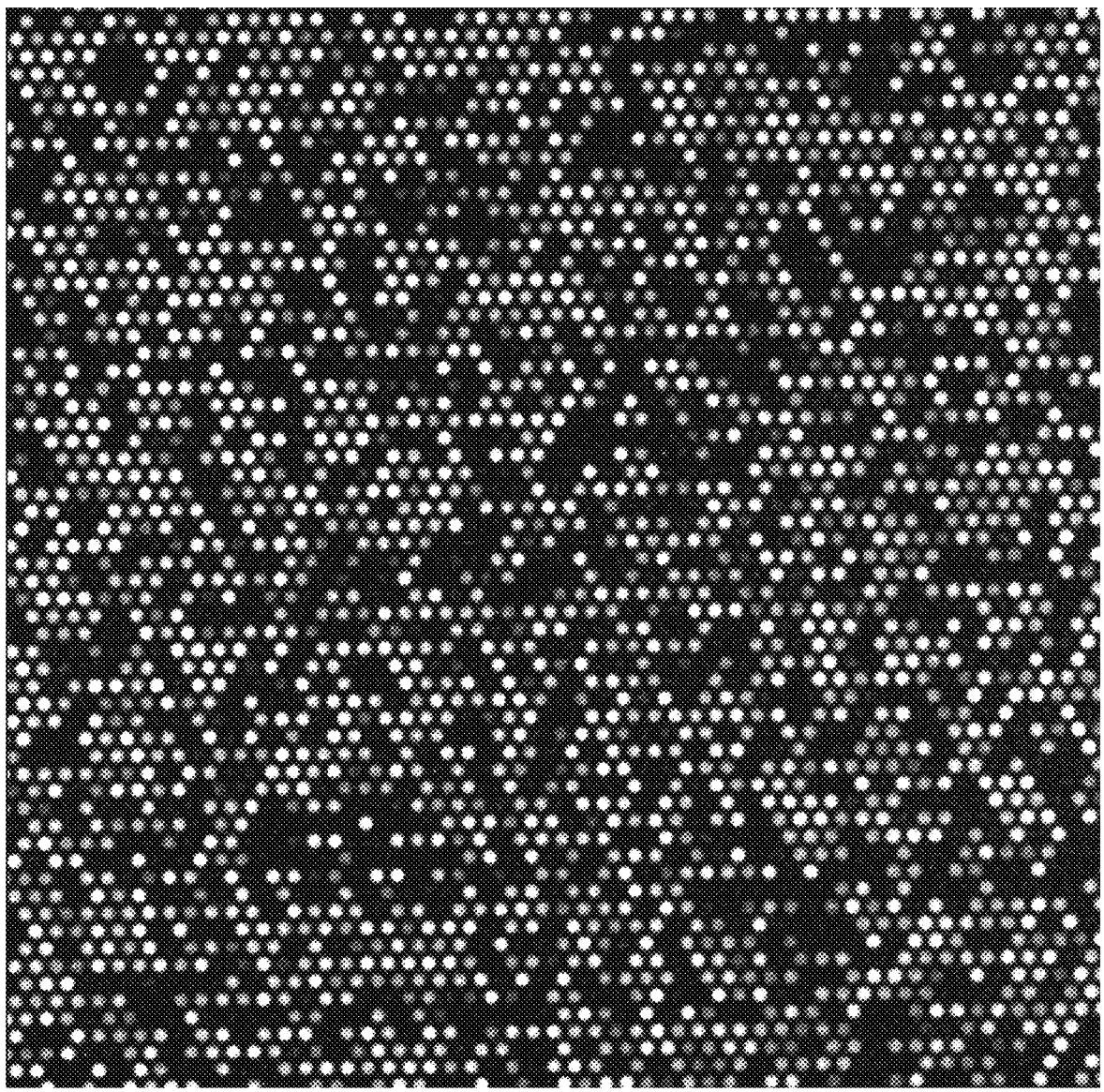
FIG. 11G is a fluorescence image showing the result of the fluorescence amount measurement test performed in the second example of the present invention under the conditions of a concentration of TWEEN 20 of 5% and a heating time of 10 minutes.
Figure 11H:
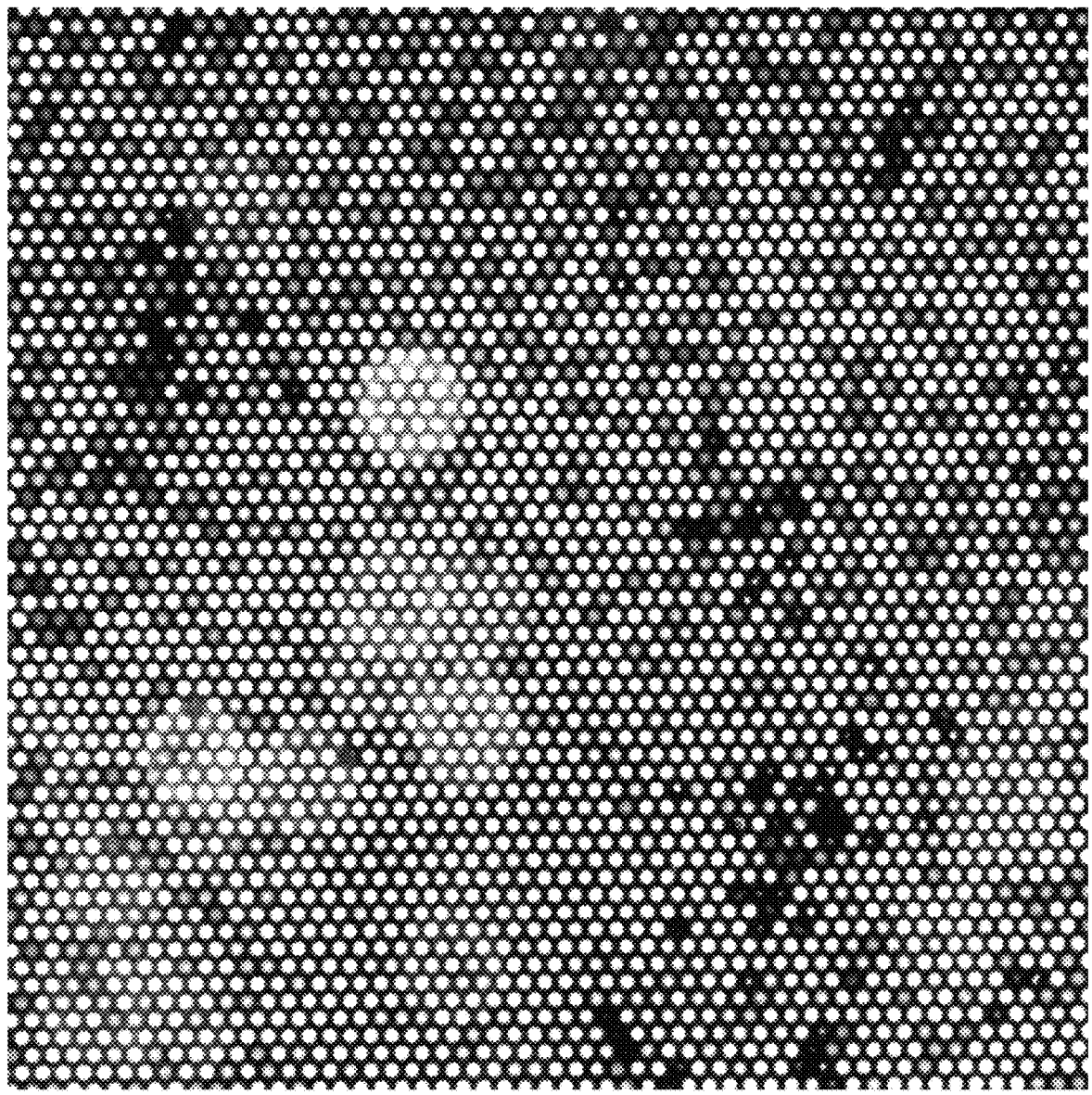
FIG. 11H is a fluorescence image showing the result of the fluorescence amount measurement test performed in the second example of the present invention under the conditions of a concentration of TWEEN 20 of 0.0005% and a heating time of 20 minutes.
Figure 11I:
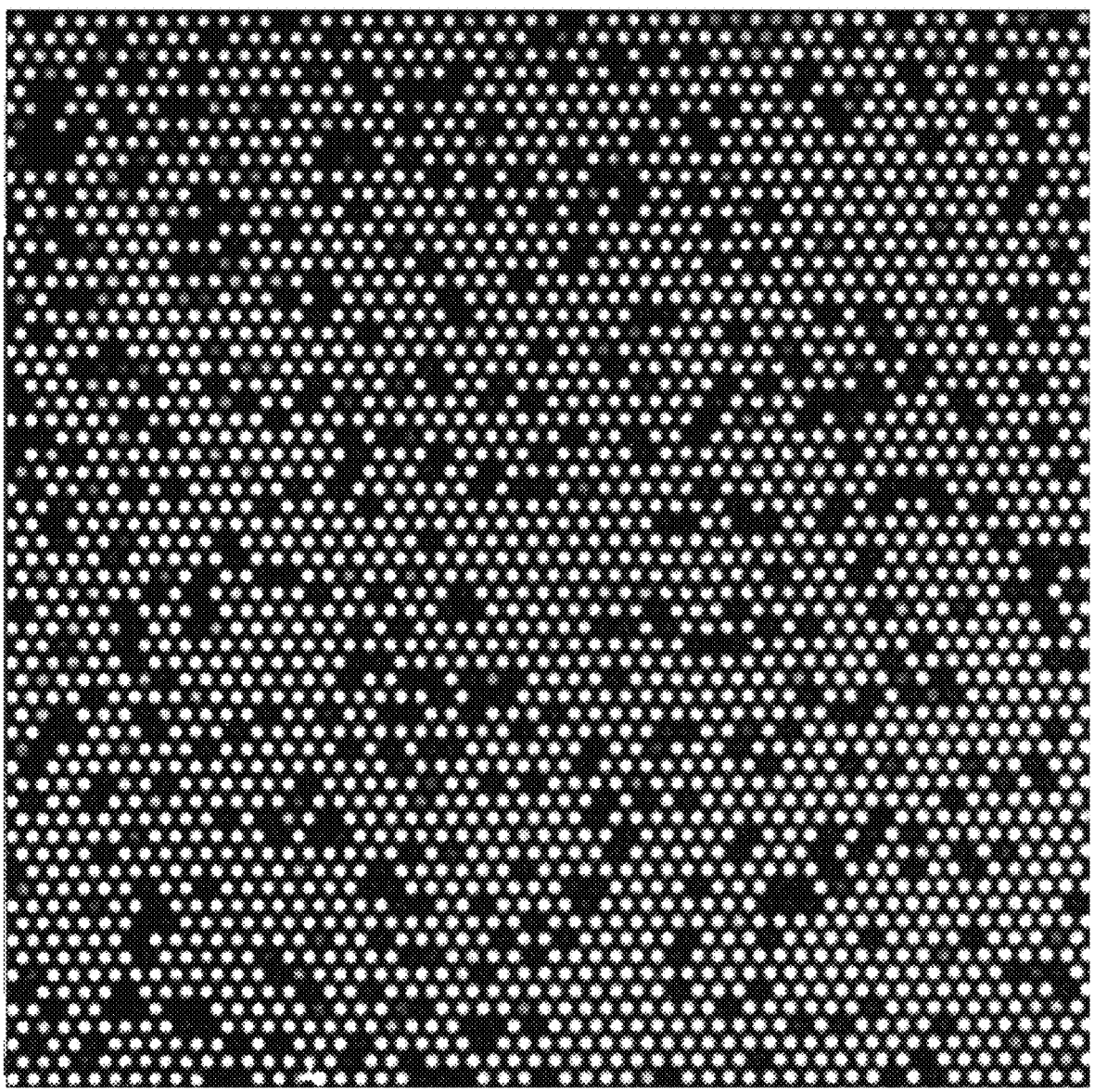
FIG. 11I is a fluorescence image showing the result of the fluorescence amount measurement test performed in the second example of the present invention under the conditions of a concentration of TWEEN 20 of 0.001% and a heating time of 20 minutes.
Figure 11J:
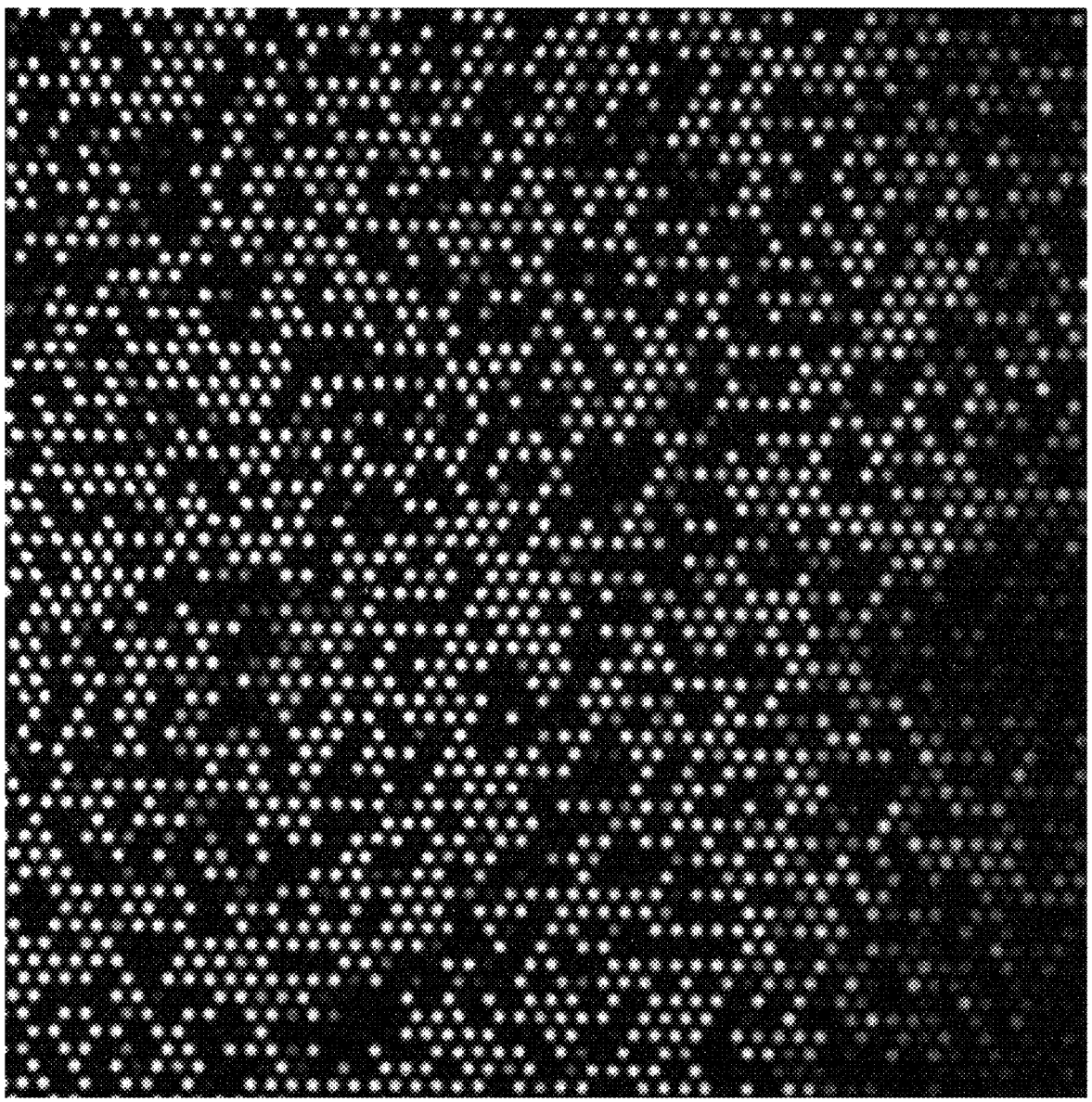
FIG. 11J is a fluorescence image showing the result of the fluorescence amount measurement test performed in the second example of the present invention under the conditions of a concentration of TWEEN 20 of 0.005% and a heating time of 20 minutes.
Figure 11K:
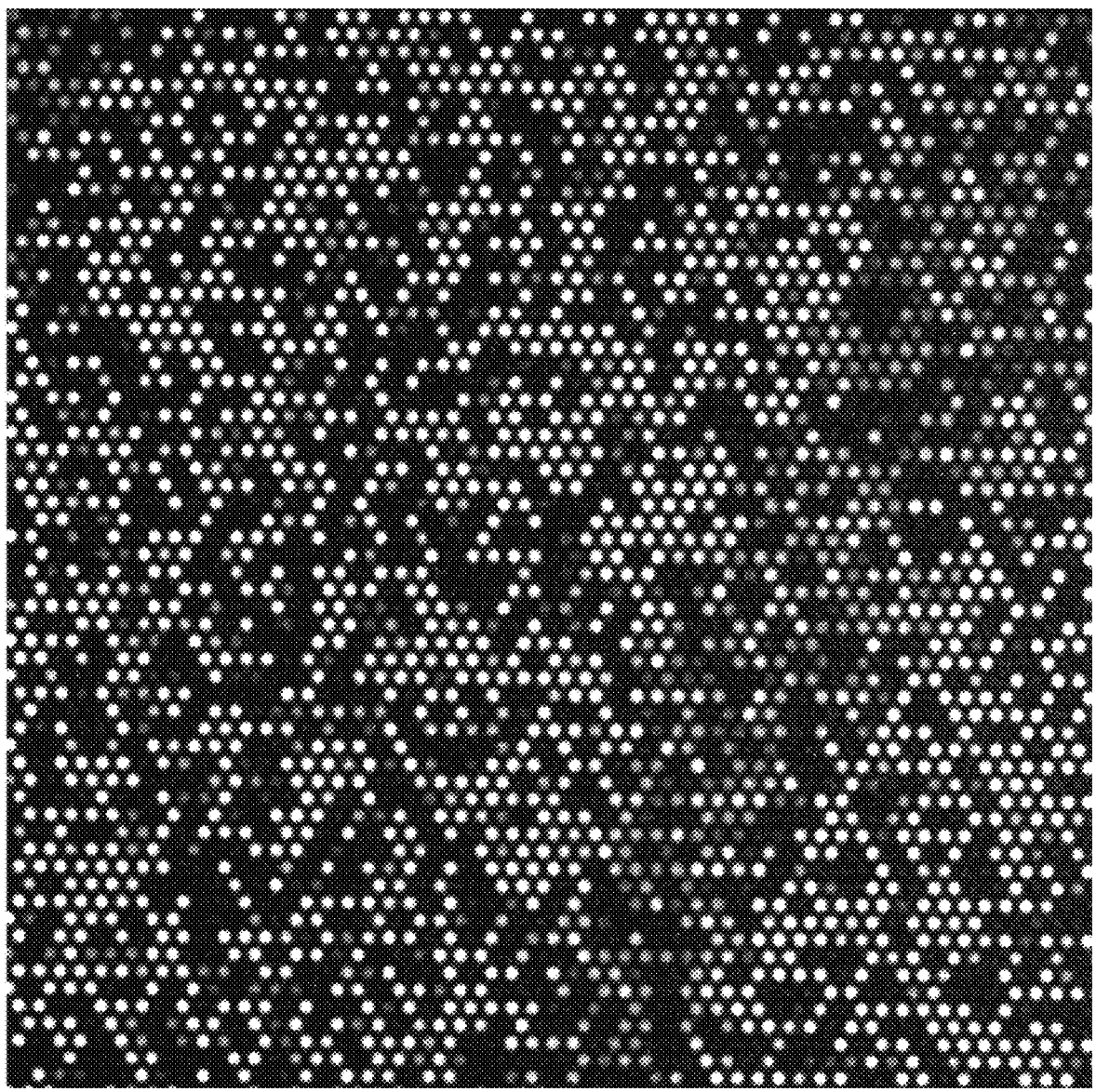
FIG. 11K is a fluorescence image showing the result of the fluorescence amount measurement test performed in the second example of the present invention under the conditions of a concentration of TWEEN 20 of 0.05% and a heating time of 20 minutes.
Figure 11L:
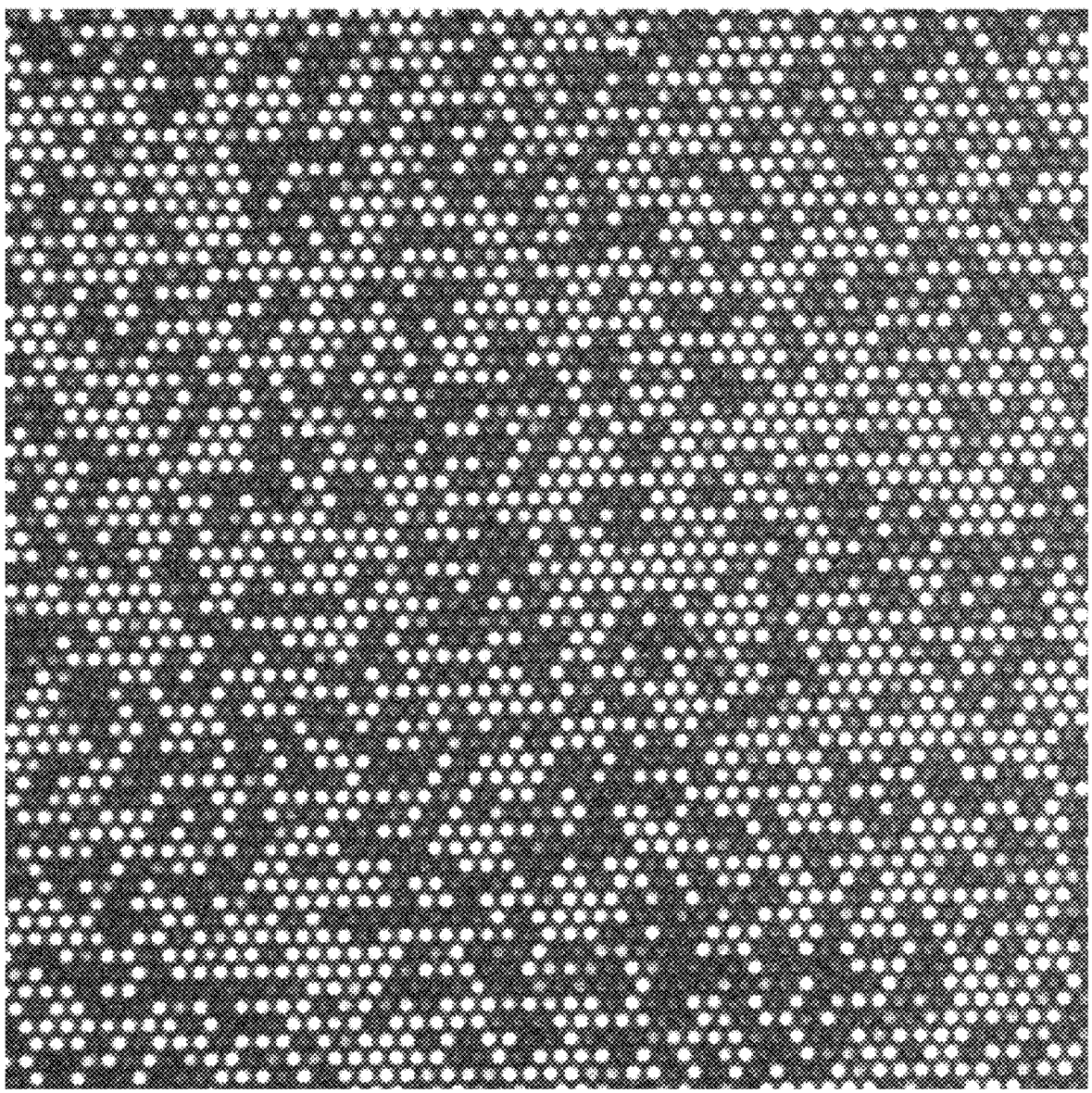
FIG. 11L is a fluorescence image showing the result of the fluorescence amount measurement test performed in the second example of the present invention under the conditions of a concentration of TWEEN 20 of 0.5% and a heating time of 20 minutes.
Figure 11M:
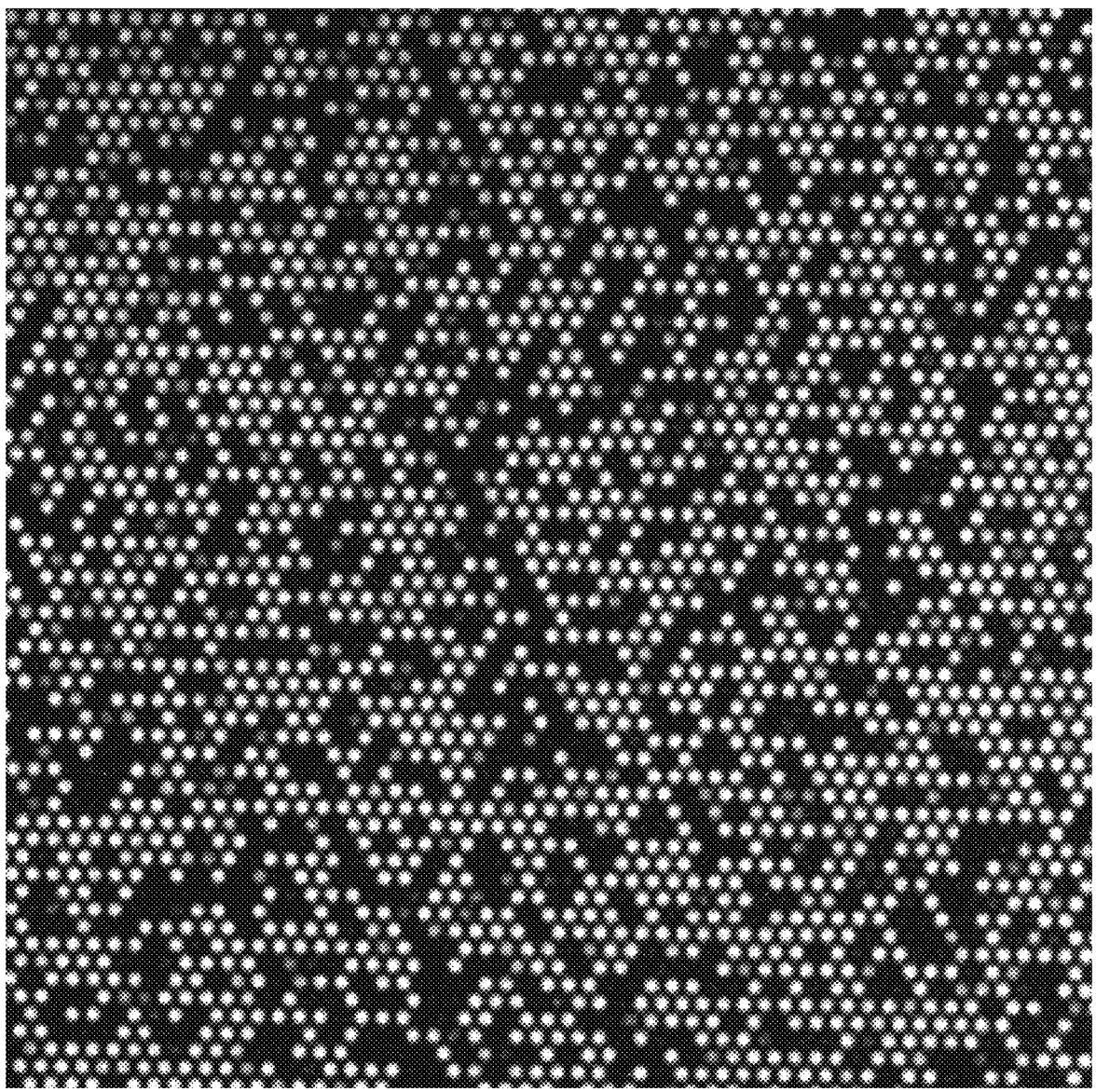
FIG. 11M is a fluorescence image showing the result of the fluorescence amount measurement test performed in the second example of the present invention under the conditions of a concentration of TWEEN 20 of 5% and a heating time of 20 minutes.
Figure 14A:
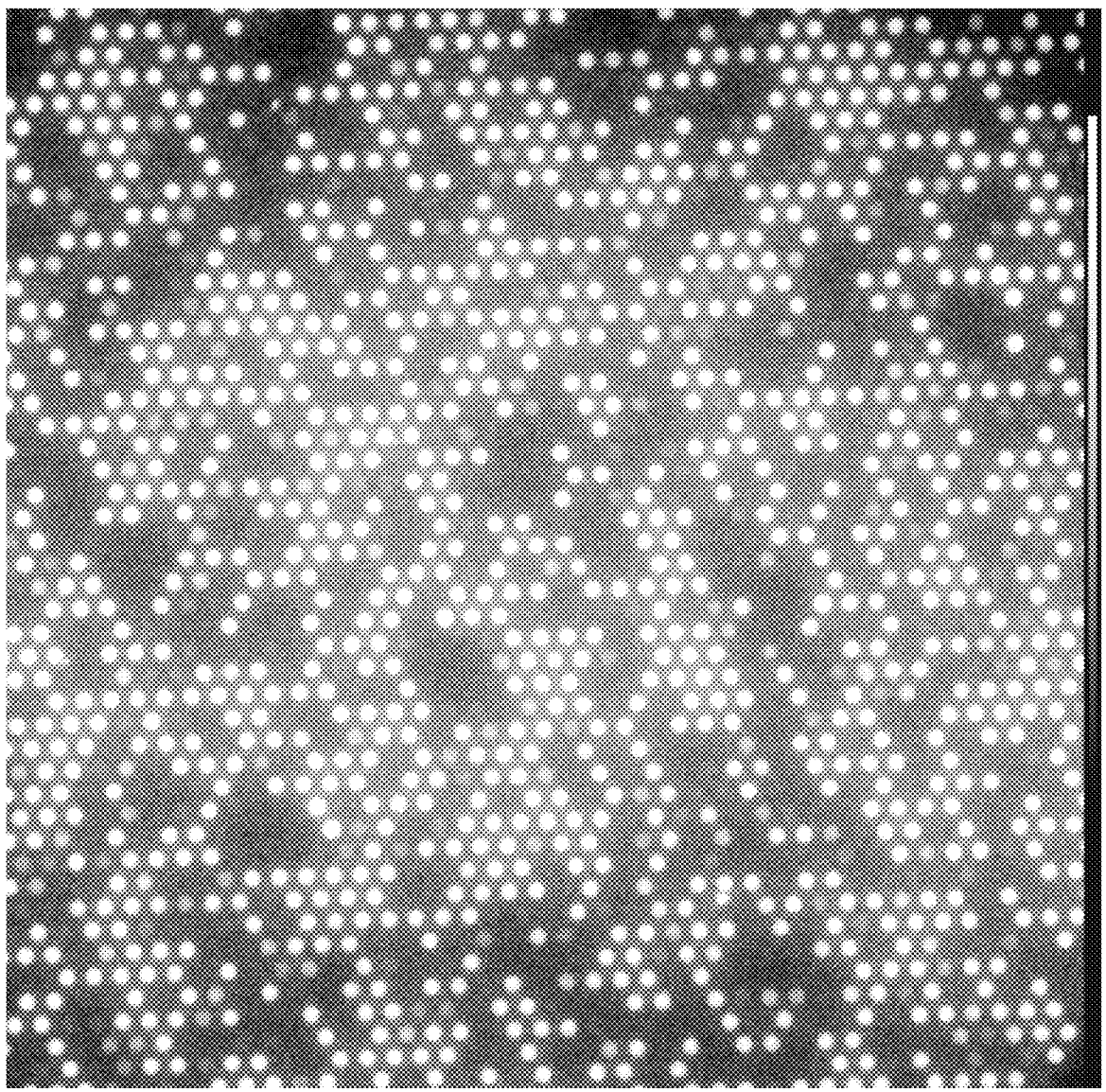
FIG. 14A is a fluorescence image showing the result of a fluorescence amount measurement test on a sample 1 in a third example of the present invention.
Figure 14B:
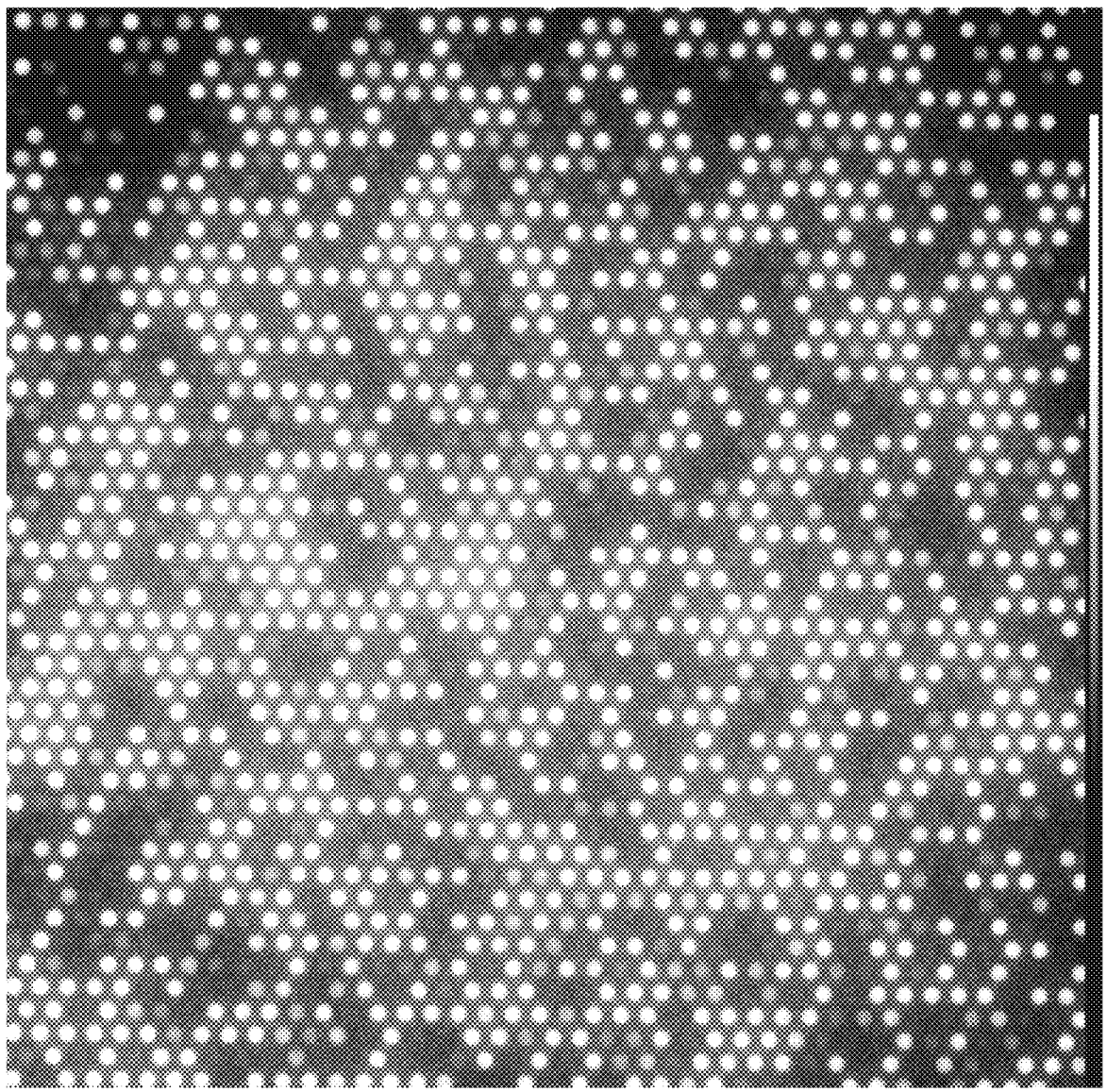
FIG. 14B is a fluorescence image showing the result of a fluorescence amount measurement test on a sample 2 in the third example of the present invention.
Figure 14C:
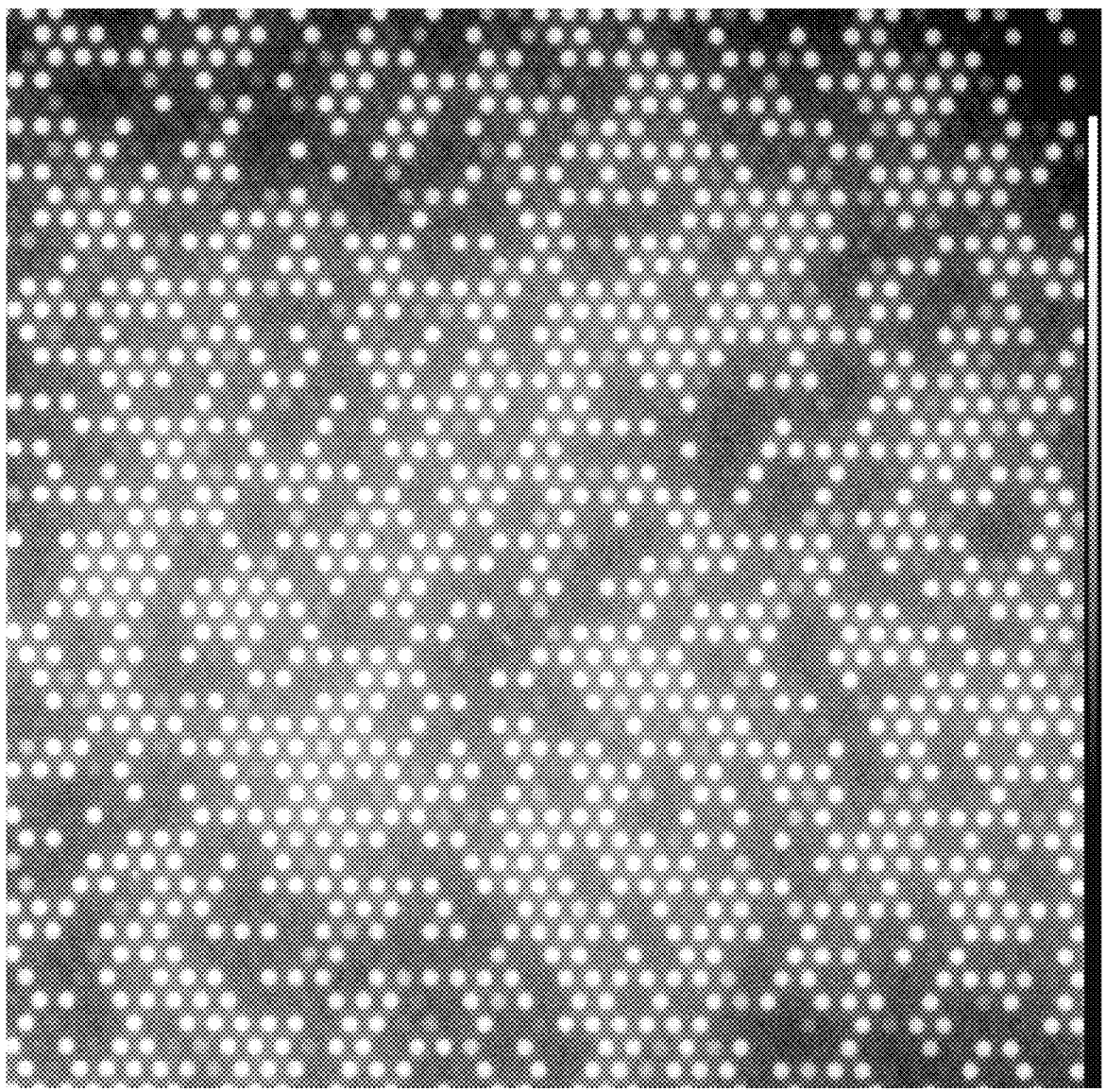
FIG. 14C is a fluorescence image showing the result of a fluorescence amount measurement test on a sample 3 in the third example of the present invention.
Figure 14D:
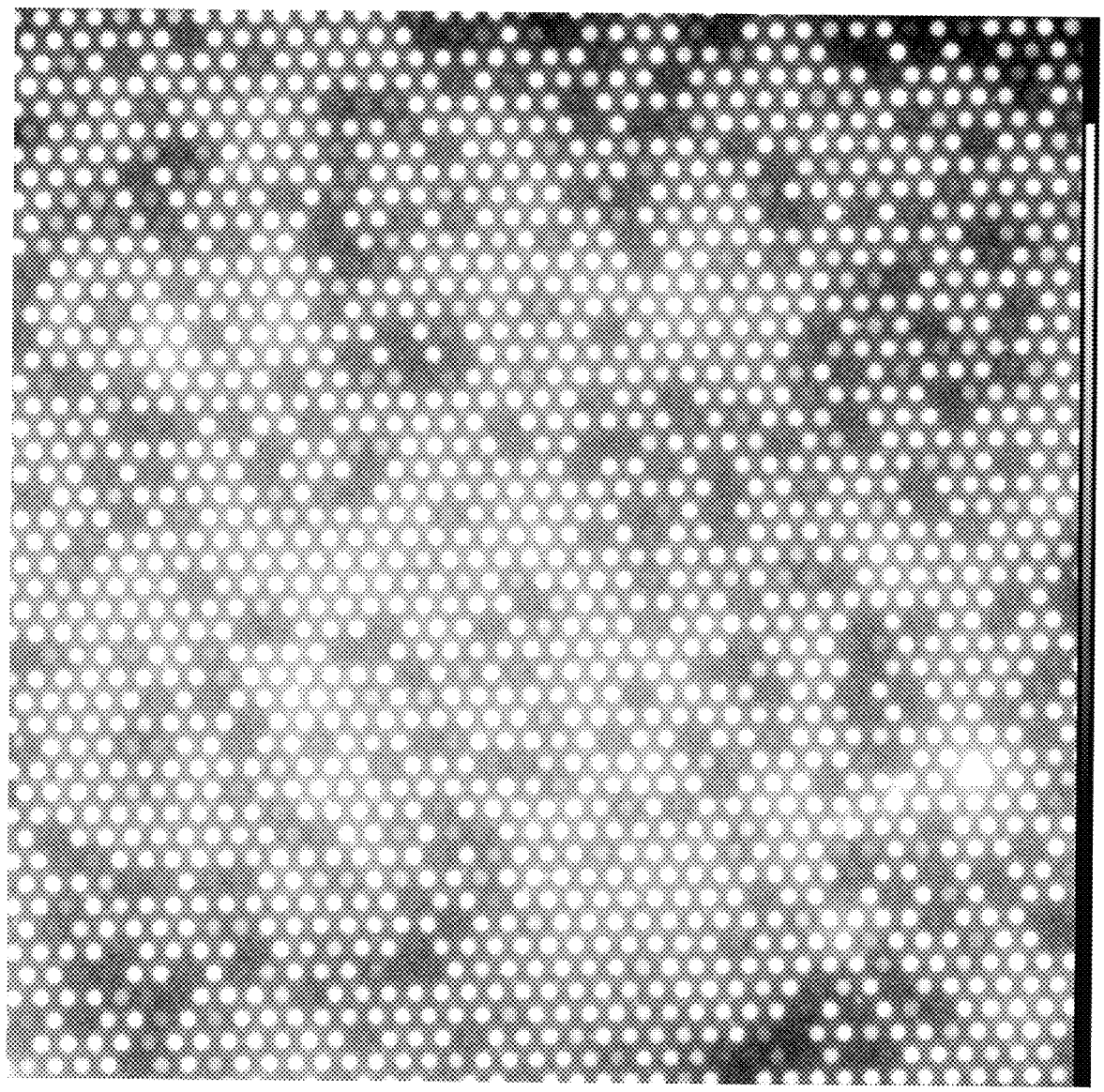
FIG. 14D is a fluorescence image showing the result of a fluorescence amount measurement test on a sample 4 in the third example of the present invention.
Figure 14E:
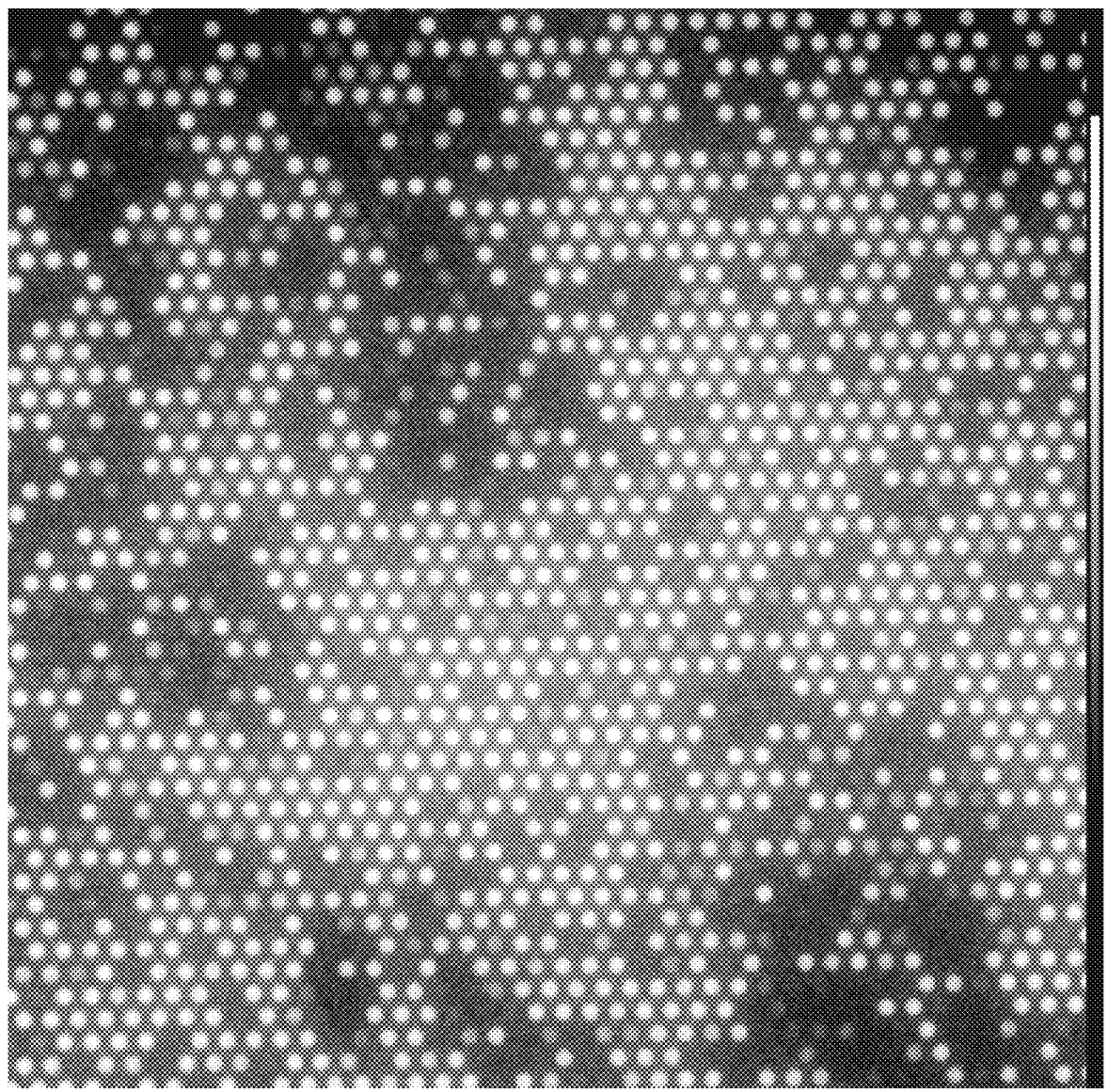
FIG. 14E is a fluorescence image showing the result of a fluorescence amount measurement test on a sample 5 in the third example of the present invention.
Figure 14F:
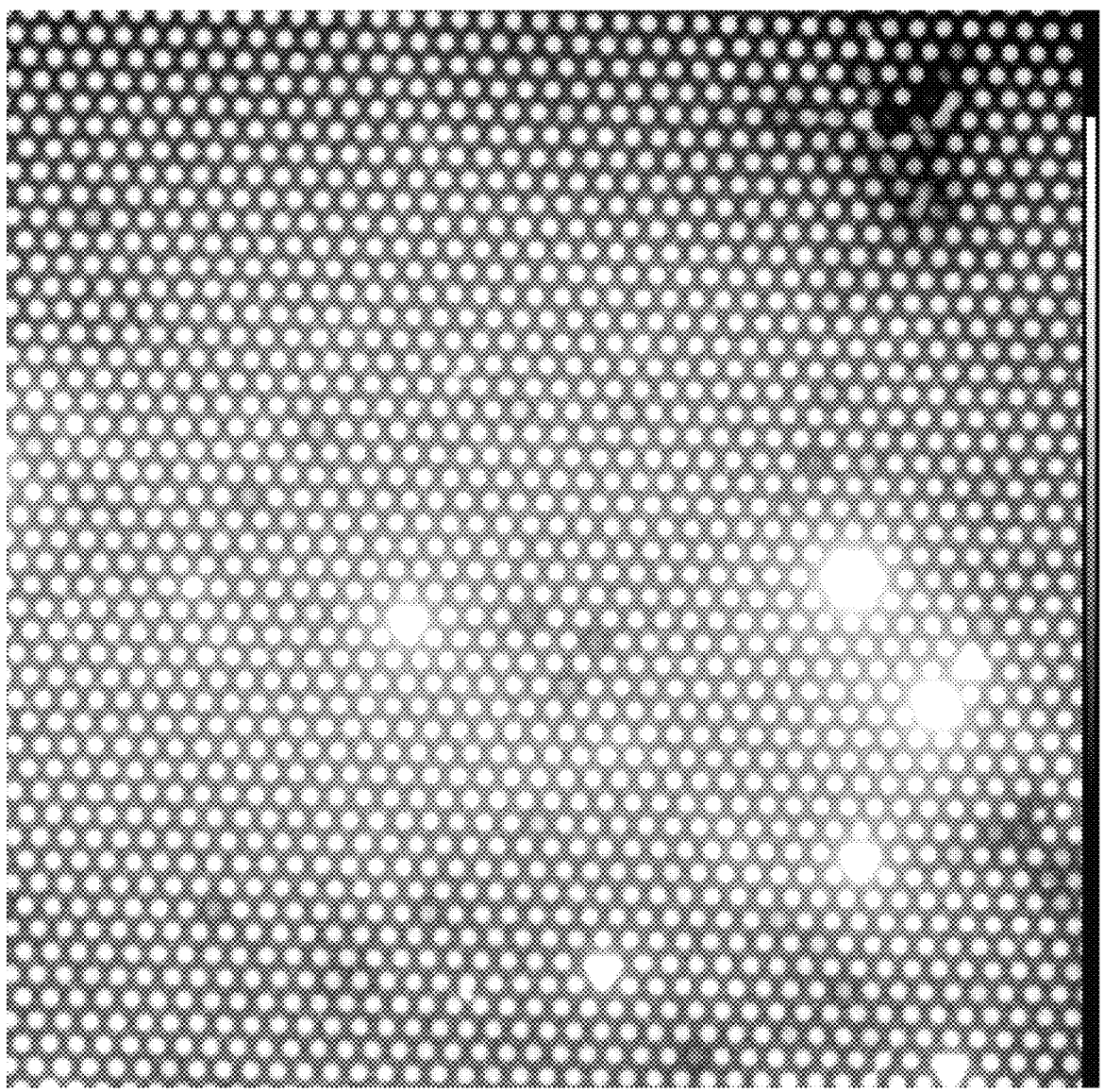
FIG. 14F is a fluorescence image showing the result of a fluorescence amount measurement test on a sample 6 in the third example of the present invention.

Next, an example demonstrated for checking the operation and effect of the biomolecule analysis method according to the second embodiment of the present invention will be described. FIG. 10 is a fluorescence image showing wells in the present example. FIGS. 11A to 11M are fluorescence images showing the results of a fluorescence amount measurement test in the present example. FIG. 12 is a graph showing the results of a fluorescence intensity measurement test in the present example. In FIG. 12, the abscissa shows the concentration of TWEEN 20, and the ordinate shows the fluorescence intensity.

<Preparation of Array Device for Nucleic Acid Quantification>

A glass substrate having a thickness of 0.5 mm was spin-coated with CYTOP (registered trademark) (manufactured by ASAHI GLASS CO., LTD.) and then baked for 1 hour at 180° C. The thickness of the formed CYTOP was 3 µm. After being spin-coated with CYTOP, the substrate was coated with a positive photoresist, and a pattern was formed thereon by using a photomask. Then, by using 02 plasma, CYTOP was dry-etched. In order to remove the residual photoresist on the surface, the surface was washed and rinsed with acetone and ethanol.

As shown in FIG. 10, each of the wells (microspaces) formed of CYTOP had a diameter of 5 µm and had a volume that makes it possible to detect a signal within several minutes by the INVADER reaction. In a single base portion, a well array consisting of 100 blocks was provided, and each of the blocks had 10,000 wells. Therefore, a total of 1,000,000 wells were formed. As shown in FIG. 6, a glass plate having a feeding port (inlet portion: not shown in the drawing) was bonded to the base portion by using a double-sided tape which had a thickness of 50 µm and was processed to have a flow channel shape.

<Feeding Mixed Liquid of Sample and Detection Reaction Reagent>

The ease of forming liquid droplets by the concentration of TWEEN 20 as a surfactant was checked.

First, through the feeding port, a wash buffer containing the surfactant was fed into the array device for nucleic acid quantification. Then, 22 µl of an INVADER reaction reagent (detection reaction reagent 21: 1 µM allele probe, 1 µM INVADER oligo, 1 µM FAM-labeled arm, 10 mM MOPS pH 7.5, 6.25 mM $MgCl_2$, 50 U/µL cleavase, TWEEN 20) and DNA which was a substance as a target of analysis were fed into the array device for nucleic acid quantification.

Thereafter, through the feeding port, 80 µl of FC40 (oleaginous sealing solution 22) as a fluorine-based liquid was fed into the array device such that the reagent was distributed into and filled the respective wells. By heating the array device on a hot plate at 63° C., the INVADER reaction was performed.

Subsequently, by using a fluorescence microscope (manufactured by OLYMPUS CORPORATION), at points in time when 10 minutes and 20 minutes elapsed at 63° C., the fluorescence from each well was detected. The exposure time was set to be 100 msec for a bright field, 2,000 msec for NIBA, and 2,000 msec for mCherry.

FIGS. 11A to 11G show the results obtained by observing each well with a microscope after 10 minutes of heating. FIGS. 11H to 11M shows the results obtained by observing each well with a microscope after 20 minutes of heating.

When the concentration of TWEEN 20 was 0%, fluorescence was also detected from the region positioned between the adjacent wells, and accordingly, digital measurement could not be accurately performed. Presumably, this is because the droplets of the reaction solution in the adjacent wells were bonded to each other, and thus the sample reacted in the region positioned between the adjacent wells. As another reason, it is considered that although the droplets of the reaction solution in the adjacent wells were not bonded to each other, the residual sample on the surface of the base portion positioned between the adjacent wells reacted. In contrast, it was confirmed that if the concentration of TWEEN 20 contained is equal to or greater than 0.0005%, the droplets of the reaction solution are separated from each other.

Furthermore, it was confirmed that if the concentration of TWEEN 20 contained is equal to or greater than 0.001% in the wells having undergone 20 minutes of heating, the droplets of the reaction solution are separated from each other. That is, it is considered that in a case where heating is performed for a long period of time, if the concentration of TWEEN 20 contained is equal to or greater than 0.001%, the reproducibility is further improved compared to a case where heating is performed for a short period of time.

FIG. 12 is a graph showing the values of fluorescence intensity associated with the concentration of TWEEN 20. As the concentration of TWEEN 20 increased, the fluorescence intensity weakened. That is, a behavior in which the increase in the concentration of TWEEN 20 hindered the reaction was confirmed. Therefore, an optimal concentration of TWEEN 20 is assumed to be less than about 5%. In addition, it is considered that, from the viewpoint of costs, the concentration of TWEEN 20 is more preferably equal to or less than 0.5%.

10 µl of the same reagent was dispensed into a 96-well plate, and the reactivity at a volume of 10 µl was detected using LightCycler LC480 (manufactured by Roche Life Science). The temperature condition of the LightCycler was kept constant at 63° C. With the LightCycler, a reaction was performed in the same composition as described above. As a result, it was confirmed that the increase of the fluorescence signal of the INVADER reaction was constant regardless of the concentration of TWEEN 20. Therefore, it was understood that the surfactant contributes not to the improvement of the reactivity of the enzyme but to the stability of the liquid droplets.

The surfactant should be added at such a concentration that can prevent the substance as a target of detection contained in the reagent from being adsorbed onto CYTOP, glass, or the like. In a case where other surfactants such as TRITON-X100 are used, the optimal concentration may be changed, but the case of TWEEN 20 can be taken into consideration.

Third Example

Next, an example demonstrated for checking the operation and effect of the biomolecule analysis method according to the second embodiment of the present invention will be described. FIG. 13 is a view showing the operation and effect of the biomolecule analysis method according to the second embodiment of the present invention. FIGS. 14A to 14F are fluorescence images showing the results of a fluorescence amount measurement test in the present example. In FIG. 13, "Excellent" in the column of reactivity means that the reactivity is excellent, and "O" in the column of liquid droplet means that fluorescence was not observed in the region between two adjacent wells. Furthermore, in FIG. 13, "A" in the column of liquid droplet means that, although fluorescence was observed in the region between two adjacent wells, the measurement of concentration was not affected by the fluorescence. In addition, in FIG. 13, "X" in the column of liquid droplet means that fluorescence was observed in the region between two adjacent wells, and thus the digital measurement could not be accurately performed in some cases when the region between the two adjacent wells is used.

In the present example, by using the INVADER reaction reagent and DNA used in the second example, as shown in FIG. 13, a reaction was performed by changing the conditions such as whether or not the well will be washed, whether or not a surfactant will be added to the wash buffer, and whether or not a surfactant will be added to the reaction reagent, and from the obtained fluorescence image, the state and reactivity of the liquid droplets were checked. As a surfactant, 0.05% TWEEN 20 was added to the wash buffer or the reaction reagent. Other conditions were the same as in the second example.

In samples 1 and 2, the wells were washed by adding the surfactant to the wash buffer. In samples 3 and 4, the wells were washed without adding the surfactant to the wash buffer. In samples 5 and 6, the wells were not washed. Furthermore, the surfactant was added to the reaction reagent for the samples 1, 3, and 5. In contrast, the surfactant was not added to the reaction reagent for the samples 2, 4, and 6. The reactivity was excellent in all of the samples. In addition, as is evident from the sample 2, it was understood that, even in a case where the surfactant is not added to the reaction reagent, as long as the wash buffer contains the surfactant, liquid droplets are excellently formed, and the reactivity becomes excellent.

As described above, with the biomolecule analysis method and the biomolecule analysis kit 100 according to the first embodiment of the present invention and with the biomolecule analysis method and the biomolecule analysis kit 100A according to the second embodiment of the present invention, it is possible to rapidly and quantitatively analyze biomolecules by performing an enzymatic reaction in the microspaces 11 or the wells 26.

In the biomolecule analysis method and the biomolecule analysis kit 100 according to the first embodiment of the present invention and with the biomolecule analysis method and the biomolecule analysis kit 100A according to the second embodiment of the present invention, an INVADER method is used as an enzymatic reaction. As a result, PCR amplification is not required, and an isothermal reaction can be performed. Therefore, the device constitution and the analysis procedure can be simplified.

In the biomolecule analysis method and the biomolecule analysis kit 100 according to the first embodiment of the present invention and in the biomolecule analysis method and the biomolecule analysis kit 100A according to the second embodiment of the present invention, a reaction is performed in the microspaces 11 and the wells 26 each of which has a volume to accommodate a single molecule as a target of analysis. Therefore, the time taken until the signal is saturated can be shortened.

In the biomolecule analysis method and the biomolecule analysis kit 100 according to the first embodiment of the present invention and in the biomolecule analysis method and the biomolecule analysis kit 100A according to the second embodiment of the present invention, the reaction time is shorter and the SN ratio is higher, compared to the related art.

In the biomolecule analysis method and the biomolecule analysis kit 100 according to the first embodiment of the present invention and in the biomolecule analysis method and the biomolecule analysis kit 100A according to the second embodiment of the present invention, the enzymatic reaction is an isothermal reaction. Therefore, the enzymatic reaction that is more stable compared to a nonisothermal reaction can be carried out, and the reproducibility is high.

In the biomolecule analysis method and the biomolecule analysis kit 100 according to the first embodiment of the present invention and in the biomolecule analysis method and the biomolecule analysis kit 100A according to the second embodiment of the present invention, the enzymatic reaction is an INVADER reaction. Therefore, the time taken for signal detection/determination can be further shortened compare to the process requiring PCR.

In the biomolecule analysis method and the biomolecule analysis kit 100 according to the first embodiment of the present invention and in the biomolecule analysis method and the biomolecule analysis kit 100A according to the second embodiment of the present invention, each of the microspaces 11 or the wells 26 has a volume of equal to or less than 100 picoliters. Therefore, the amount of the reagent consumed for analysis can be reduced.

In the above embodiments, examples in which the low-adsorption structural portion and the adsorption inhibitor are used in combination are described. However, as long as at least one of the low-adsorption structural portion and the adsorption inhibitor is adopted, it is possible to more rapidly and quantitatively analyze biomolecules compared to a case where none of the low-adsorption structural portion and the adsorption inhibitor is adopted.

What is claimed is:

1. A biomolecule analysis kit comprising:
an array device including:
  a base portion being a flat plate,
  a reaction container configured to perform an enzymatic reaction, the reaction container including a plurality of wells to which sample biomolecules as targets of biomolecule analysis is to be supplied, the plurality of wells being formed in the base portion,
  a flat cover portion superposed on the base portion and the plurality of wells,
  a flow channel formed between the flat cover portion and the plurality of wells and connecting the plurality of wells through a gap between the base portion and the flat cover portion, the flow channel having:
  an inlet portion, and
  an outlet portion, wherein at least one well among the plurality of wells is positioned between the inlet portion and the outlet portion; and
a reagent configured to be supplied to the plurality of wells and to be used for the enzymatic reaction which generates a signal, wherein
  the reagent contains an adsorption inhibitor to reduce an adsorption rate of at least one of the sample biomolecules or the reagent with respect to the base portion; and
  the base portion has a hydrophobic surface at a region positioned between wells that are adjacent, among the plurality of wells.

2. The biomolecule analysis kit according to claim 1, wherein
the adsorption inhibitor is a surfactant.

3. The biomolecule analysis kit according to claim 2, wherein
the surfactant is a nonionic surfactant.

4. The biomolecule analysis kit according to claim 3, wherein
the nonionic surfactant is polyethylene glycol sorbitan monolaurate.

5. The biomolecule analysis kit according to claim 3, wherein
the nonionic surfactant is 4-(1,1,3,3-Tetramethylbutyl) phenyl-polyethylene glycol.

6. The biomolecule analysis kit according to claim 2, wherein
the concentration of the surfactant is equal to or greater than 0.0005 vol % and equal to or less than 5 vol %.

7. The biomolecule analysis kit according to claim 1, further comprising:
an oil sealing solution configured to seal each of the plurality of wells filled with the reagent.

8. The biomolecule analysis kit according to claim 7, wherein
the oil sealing solution is configured to cover each of the plurality of wells and the hydrophobic surface.

9. The biomolecule analysis kit according to claim 1, wherein
the volume of each well of the wells is equal to or less than 100 picoliters.

10. The biomolecule analysis kit according to claim 1, further comprising:
a wash buffer to be fed into the gap between the base portion and the flat cover portion.

11. The biomolecule analysis kit according to claim 10, wherein
the wash buffer contains an adsorption inhibitor.

12. The biomolecule analysis kit according to claim 10, wherein
the wash buffer is intermixable with the reagent.

13. The biomolecule analysis kit according to claim 1, further comprising:
a wash buffer filled in the gap between the base portion and the flat cover portion.

14. The biomolecule analysis kit according to claim 13, wherein
the wash buffer contains an adsorption inhibitor.

15. The biomolecule analysis kit according to claim 13, wherein
the wash buffer is intermixable with the reagent.

16. The biomolecule analysis kit according to claim 1, wherein
the base portion is transparent.

* * * * *